(12) United States Patent
Reginald et al.

(10) Patent No.: US 12,029,763 B2
(45) Date of Patent: Jul. 9, 2024

(54) IMMUNO-MODULATORY PROGENITOR (IMP) CELL

(71) Applicant: CELL THERAPY LIMITED, Swansea (GB)

(72) Inventors: Ajan Reginald, Swansea (GB); Martin John Evans, Swansea (GB); Sabena Sultan, Swansea (GB)

(73) Assignee: CELL THERAPY LIMITED (GB)

( * ) Notice: Subject to any disclaimer, the term of this patent is extended or adjusted under 35 U.S.C. 154(b) by 0 days.

(21) Appl. No.: 14/904,411

(22) PCT Filed: Jun. 9, 2015

(86) PCT No.: PCT/GB2015/051673
§ 371 (c)(1),
(2) Date: Jan. 11, 2016

(87) PCT Pub. No.: WO2015/189587
PCT Pub. Date: Dec. 17, 2015

(65) Prior Publication Data
US 2017/0080029 A1 Mar. 23, 2017

(30) Foreign Application Priority Data
Jun. 12, 2014 (GB) .................................. 1410504

(51) Int. Cl.
*A61K 35/28* (2015.01)
*C12N 5/071* (2010.01)
*C12N 5/0775* (2010.01)
*C12N 5/078* (2010.01)

(52) U.S. Cl.
CPC ............ *A61K 35/28* (2013.01); *C12N 5/0633* (2013.01); *C12N 5/0634* (2013.01); *C12N 5/0663* (2013.01); *C12N 5/0665* (2013.01); *C12N 2500/02* (2013.01); *C12N 2500/84* (2013.01); *C12N 2500/90* (2013.01); *C12N 2506/1353* (2013.01)

(58) Field of Classification Search
CPC .... A61K 35/28; C12N 5/0663; C12N 5/0665; C12N 5/0633; C12N 5/0634
See application file for complete search history.

(56) References Cited

U.S. PATENT DOCUMENTS

| | | | |
|---|---|---|---|
| 5,198,357 A | 3/1993 | Holmovist et al. | |
| 2011/0123498 A1 | 5/2011 | Westenfelder | |
| 2012/0301538 A1* | 11/2012 | Gordon-Beresford | A61K 31/529 424/450 |
| 2013/0189741 A1* | 7/2013 | Meis | C12N 5/0696 435/91.2 |
| 2013/0195959 A1* | 8/2013 | Patel | A61P 17/02 424/447 |
| 2013/0302890 A1 | 11/2013 | Mouzannar | |

FOREIGN PATENT DOCUMENTS

| | | |
|---|---|---|
| GB | 1410506.8 | 12/2015 |
| WO | 2009144718 A1 | 12/2009 |
| WO | 2012052911 A1 | 4/2012 |
| WO | 2013005053 A2 | 1/2013 |

OTHER PUBLICATIONS

Reading et al, Clinical-Grade Multipotent Adult Progenitor Cells Durably Control Pathogenic T Cell Responses in Human Models of Transplantation and Autoimmunity, 2013, J Immunol 190:4542-4552*
Kassis, Isolation of mesenchymal stem cells from G-CSF-mobilized human peripheral blood using fibrin microbeads, Bone Marrow Transplantation, 2006, 37:967-976*
Doucet et al., Platelet lysates promote mesenchymal stem cell expansion: a safety substitute for animal serum in cell-based therapy applications, 2005, J Cell Physiol 205(2):228-36 (Year: 2005).*
Zhao et al (2011, Therapeutic Applications of Mesenchymal Stem/Multipotent Stromal Cells. In: Appasani K., Appasani R. (eds) Stem Cells & Regenerative Medicine. Stem Cell Biology and Regenerative Medicine. Humana Press, Totowa, NJ (Year: 2011).*
Salem et al, Mesenchymal Stromal Cells: Current Understanding and Clinical Status, 2010, Stem Cells, 28:585-596 (Year: 2010).*
Hanley et al, Efficient manufacturing of therapeutic mesenchymal stromal cells with the use of the Quantum Cell Expansion System, 2014, Cytotherapy; 16: 1048-1058, published online Epub Apr. 13, 2014 (Year: 2014).*
Schallmoser et al, Platelet-derived growth factors for GMP-compliant propagation ofmesenchymal stromal cells,2009, Bio-Medical Materials and Engineering 19: 271-276 (Year: 2009).*
Inamdar et al, Culture conditions for growth of clinical grade human tissue derived mesenchymal stem cells: comparative study between commercial serum-free media and human product supplemented media, 2013, Journal of Regenerative Medicine and Tissue Engineering 2(1): 1-12 (Year: 2013).*
Li et al, Mesenchymal stem cells suppress CD8+ T cell-mediated activation by suppressing natural killer group 2, member D protein receptor expression and secretion of prostaglandin E2, indoleamine 2, 3-dioxygenase and transforming growth factor-β, 2014, Clin Exp Immunol 178(3):516-24 (Year: 2014).*
Lin et al, Mesenchymal Stem Cells and the Origin of Ewing's Sarcoma, 2011, Sarcoma, 276463: 1-8 (Year: 2011).*
Huang et al, Differentiation of Allogeneic Mesenchymal Stem Cells Induces Immunogenicity and Limits Their Long-Term Benefits for Myocardial Repair, 2010, Circulation, 122(23): 2419-2429 (Year: 2010).*

(Continued)

*Primary Examiner* — Sharmila G Landau
*Assistant Examiner* — Stephanie A McNeil
(74) *Attorney, Agent, or Firm* — Norton Rose Fulbright US LLP

(57) ABSTRACT

The invention relates to immuno-modulatory progenitor (IMP) cells and their use in therapy.

3 Claims, No Drawings

(56) References Cited

OTHER PUBLICATIONS

Hemeda et al, Heparin concentration is critical for cell culture with human platelet lysate 2013, Cytotherapy, 15:1174-1181 (Year: 2013).*
Lange et al, Platelet lysate for rapid expansion of human mesenchymal stromal cells, 2008, Citation: Cellular Therapy and Transplantation, 1(2): 49-53 (Year: 2008).*
Basu et al, Purification of specific cell population by fluorescence activated cell sorting (FACS), 2010, J. Vis. Exp. (41), e1546 (Year: 2010).*
Han et al, Immunosuppressive mechanisms of embryonic stem cells and mesenchymal stem cells in alloimmune response, 2011, Transplant Immunology 25: 7-15 (Year: 2011).*
Carrancio et al., "Optimization of mesenchymal stem cell expansion procedures by cell separation and culture conditions modification", Experimental Hematology, 2008, vol. 36, pp. 1014-1021.
Iudicone et al., "Pathogen-free, plasma-poor platelet lysate and expansion of human mesenchymal stem cells", Journal of Translational Medicine, 2014, 12:28, pp. 1-14.
Zaim et al., "Donor age and long-term culture affect differentiation and proliferation of human bone marrow mesenchymal stem cells", Ann Hematol, 2012, vol. 91, pp. 1175-1186.
Humphries, "Cell Adhesion Assays", Methods in Molecular Biology, 2009, vol. 552, pp. 203-210.
Muller & Luscinskas, "Assays of Transendothelial Migration in vitro", Methods Enzymol , 2008, vol. 443, pp. 155-176.
Auerback et al., "Angiogenesis Assays: A Critical Overview", Clinical Chemistry, 2003, 49:1, pp. 32-40.
Akbarzadeh et al., "Liposome: classification, preparation, and applications", Nanoscale Research Letters, 2013, 8;102, pp. 1-9.
Meghana et al., "Liposomes: As a Typical Drug Delivery System", International Journal of Pharmaceutical and Chemical Sciences, 2012, vol. 1, No. 1, pp. 1-10.
Sirsi & Borden, "Microbubble Compositions, Properties and Biomedical Applications", Bubble Sci Eng Technol., Nov. 2009, 1(1-2): 3-17, pp. 1-28.
Anastasiadis, et al.; Implantation of a Novel Allogeneic Mesenchymal Precursor Cell Type in Patients with Ischemic Cardiomyopathy Undergoing Coronary Artery Bypass Grafting: an Open Label Phase Ila Trial; J. of Cardiovasc. Trans. Res.; Oct. 24, 2015; Accepted Feb. 29, 2016; Published online Apr. 1, 2016.
Ipsita Roy, et al; "Freeze-Drying of Proteins: Some Emerging Concerns"; Biotechnol. Appl. Biochem. (2004) 39, 165-177.
Boozer, et al; "Global Characterization and Genomic Stability of Human MultiStem, A Multipotent Adult Progenitor Cell"; Journal of Stem Cells, vol. 4, Issue 1; 2009.
Yasuhara, et al; "Behavorial and Histological Characterization of Intrahippocampal Grafts of Human Bone Marrow-Derived Multipotent Progenitor Cells in Neonatal Rats with Hypoxic-Ischemic Injury"; Cell Transplantation, vol. 14, pp. 231-238; 2006.
Keene, Dirk C., et al; "Neural Differentiation and Incorporation of Bone Marrow-Derived Multipotent Adult Progenitor Cells after Single Cell Transplantation into Blastocyst Stage Mouse Embryos"; Cell Transplantation, vol. 12, pp. 201-213; 2003.
Jiang, Yeuhua, et al; "Pluripotency of Mesenchymal Stem Cells Derived from Adult Marrow"; Nature Publishing Group; vol. 418, Jul. 4, 2002.
Reyes, Morayma, et al; "Purification and Ex Vivo Expansion of Postnatal Human Marrow Mesodermal Progenitor Cells"; Blood, vol. 98, No. 9; Nov. 1, 2001.
HJCMDXDYPOUFDY-WHFBIAKZSA-N; Version 1; PubChem CID: 123935 (l-Alanyl-l-glutamine); Available Feb. 2, 2015; Deposit Feb. 2, 2015.
Glutamax; Version 2; PubChem CID: 123935 (I-Alanyl-I-glutamine); Modify Nov. 15, 2017.
Creating a Hypoxic Environment for Cell Culture; STEMCELL Technologies, Inc., 2019.
Saurabh Pratap Singh, et al; "Comparison of Phenotypic Markers and Neural Differentiation Potential of Multipotent Adult Progenitor Cells and Mesenchymal Stem Cells" World Journal of Stem Cells, Apr. 26, 2013; 5(2): 53-60.
Deepak M. Kalaskar, et al; "Characterization of the Interface Between Adsorbed Fibronectin and Human Embryonic Stem Cells"; Journal of Royal Society Interface; Feb. 13, 2013.
S. Gronthos, et al; "Postnatal Human Dental Pulp Stem Cells (DPSCs) in Vitro and in Vivo"; PNAS, Dec. 5, 2000; vol. 97, No. 25; 13625-13630.
Chang et al. "Sphingosine 1-Phosphate Receptors Negatively Regulate Collagen Type I/III Expression in Human Bone Marrow? derived Mesenchymal Stem Cell", Journal of Cellular Biochemistry, (2014). 115(2), 359-367.
Li et al., Mesenchymal stem cells suppress CDS+ T cell-mediated activation by suppressing natural killer group 2, member D protein receptor expression and secretion of prostaglandin E2, indoleamine 2, 3-dioxygenase and transforming growth factor-[3, 2014, Clin Exp Immunol 178(3):516-24 (Year: 2014).
Mindaye et al. "Improved proteomic profiling of the cell surface of culture-expanded human bone marrow multipotent stromal cells", Journal of proteomics, (2013) 78, 1-14.
Carrancio, Soraya, et al; "Optimization of Mesenchymal Stem Cell Expansion Procedures by Cell Separation and Culture Conditions Modification"; Experimental Hemotology 2008; 36: 1014-1021.
Reinisch, Andreas, et al; "Humanized System to Propagate Cord Blood-Derived Multipotent Mesenchymal Stromal Cells for Clinical Application"; Future Medicine Ltd., ISSN 1746-0751; 2007; 2(4), 371-382.
Bieback, Karen, et al; "Human Alternatives to Fetal Bovine Serum for the Expansion of Mesenchymal Stromal Cells from Bone Marrow"; StemCells.com; Translational and Clinical Research; 2009; 27:2331-2341.
Kohn, David H., "Effects of pH on Human Bone Marrow Stromal Cells in vitro: Implications for Tissue Engineering of Bone"; 2002—Journal of Biomedical Materials Research—Wiley Online Library.
Doucet, Christelle, et al; "Platelet Lysates Promote Mesenchymal Stem Cell Expansion: A Safety Substitute for Animal Serum in Cell-Based Therapy Applications": Journal of Cellular Physiology, 205:228-236 (2005).
Schallmoser, Katharina, et al; "Preparation of Pooled Human Platelet Lysate (pHPL) as an Efficient Supplement for Animal Serum-Free Human Stem Cell Cultures"; Journal of Visualized Experiments; www.jove.com; 2009; 1-4.
Schallmoser, Katharina, et al; "Human Platelet Lysate can Replace Fetal Bovine Serum for Clinical-Scale Expansion of Functional Mesencymal Stromal Cells"; Transplatation and Cellular Engineering; Transfusion; vol. 47, Aug. 2007.
Schallmoser, Katharina, et al; "Rapid Large-Scale Expasion of Multifunctional Mesenchymal Stem Cells from Unmanipulated Bone Marrow without Animal Serum": Tissue Engineering: Cpat C; vol. 14, No. 3; 2008.
Reinisch, Andreas, et al; "Humanized Large-Scale Expanded Endothelial Colony-Forming Cells Function in vitro and in vivo": Blood. Jun. 25, 2009; 113(26): 6716-6725.
Lange, Claudia, et al; "Accelerated and Safe Expansion of Human Mesenchymal Stromal Cells in Animal Serum-Free Medium for Transplatation and Regenerative Medicine"; Journal of Cellular Physiology; Wiley Interscience, 2007.
Bernardo, M.E., "Optimization of In Vitro Expansion of Human Multipotent Mesenchymal Stromal Cells for Cell-Therapy Approaches": Further Insights in the Search for a Fetal Calf Serum Substitute; Journal of Cellular Physiology, Wiley Interscience, 2006, pp. 121-131.
Sun, Shi-Yong; "N-Acetylcysteine, Reactive Oxygen Species and Beyond" National Institute of Health Pubic Access; Cancer Biol Ther. 2010, January; 9(2): 109-110.
Chesney et al., "The peripheral blood fibrocyte is a potent antigen-presenting cell capable of priming naive T cells in situ", Immunology, Proc. Natl. Acad. Sci. USA, vol. 94, pp. 6307-6312, Jun. 1997.
Deans and Moseley, "Mesenchymal stem cells: Biology and potential clinical uses", Experimental Hematology, 28 (2000) 875-884.

(56) References Cited

OTHER PUBLICATIONS

Le Blanc et al., "Mesenchymal Stem Cells Inhibit and Stimulate Mixed Lymphocyte Cultures and Mitogenic Responses Independently of the Major Histocompatibility Complex", Scandinavian J. of Immuno., 57, 11-20, 2003, Blackwell Publishing Ltd.

Majumdar et al., "Characterization and Functionality of Cell Surface Molecules on Human Mesenchymal Stem Cells", J Biomed Sci., 2003; 10:228-241.

Pittenger, et al., "Multilineage potential of adult human mesenchymal stem cells", Science, Apr. 2, 1999, 184, 5411, p. 143.

Stagg et al., "Interferon-γ-stimulated marrow stromal cells: a new type of nonhematopoietic antigen-presenting cell", BLOOD, Mar. 15, 2006, vol. 107, No. 6.

Tse, W. et al., "Suppression of Allogeneic T-Cell Proliferation by Human Marrow Stromal Cells: Implications In", Transplantation, Feb. 15, 2003, vol. 75, 389-397, No. 3.

Abdelrazik, et al "Mesenchymal stem cells expanded in human platelet lysate display a decreased inhibitory capacity on T- and NK-cell proliferation and function", Eur. J. Immunol., No. 41, 2011, pp. 3281-3290.

Abdi, et al (Immunomodulation by Mesenchymal Stem Cells, A Potential Therapeutic Strategy for Type 1 Diabetes, Diabetes, vol. 57, 2008, pp. 1759-1767.

Abstracts, ESGCT and FSGT Collaborative Congress, Helsinki, Finland, Human Gene Therapy, Sep. 17-20, 2015, 108 pages.

Capelli, et al "Human platelet lysate allows expansion and clinical grade production of mesenchymal stromal cells from small samples of bone marrow aspirates or marrow filter washouts", Bone Marrow Transplantation, No. 40, 2007, pp. 785-791.

English, et al "Mechanisms of mesenchymal stromal cell immunomodulation", Immunology and Cell Biology, No. 91, 2013, pp. 19-26.

International Search Report and Written Opinion from related International Application PCT/GB2015/051673, dated Oct. 9, 2015, 4 pages.

Karussis, et al "Immunomodulation and neuroprotection with mesenchymal bone marrow stem cells (MSCs): A proposed treatment for multiple sclerosis and other neuroimmunological/neurodegenerative diseases", Journal of the Neurological Sciences, No. 265, 2008, pp. 131-135.

Nauta, et al "Immunomodulatory properties of mesenchymal stromal cells", BLOOD, vol. 110, No. 10, 2007, pp. 3499-3506.

Yoo, et al "Comparison of immunomodulatory properties of mesenchymal stem cells derived from adult human tissues", Cellular Immunology, No. 259, 2009, pp. 150-156.

* cited by examiner

IMMUNO-MODULATORY PROGENITOR (IMP) CELL

This application is a national phase application under 35 U.S.C. § 371 of International Application No. PCT/GB2015/051673 filed Jun. 9, 2015, which claims priority from GB Application No. 1410504.3 filed on Jun. 12, 2014, which is incorporated herein by reference. The entire contents of each of the above—referenced disclosures is incorporated herein by reference without disclaimer.

FIELD OF THE INVENTION

The invention relates to immuno-modulatory progenitor (IMP) cells and their use in therapy.

BACKGROUND TO THE INVENTION

Mesodermal cells are derived from a number of tissues and act as the supportive structure for other cell types. Bone marrow for instance is made of both haematopoietic and mesenchymal derived cells. Two principle mesenchymal cell types have been previously described and characterized, namely (i) mesenchymal stem cells (MSCs) and their precursors and (ii) mesenchymal precursor cells (MPCs) found in the bone marrow. Mesenchymal stem cells (MSCs) are multipotent, adult stem cells. MSCs differentiate to form the different specialised cells found in the skeletal tissues. For example, they can differentiate into cartilage cells (chondrocytes), bone cells (osteoblasts) and fat cells (adipocytes).

MSCs are used in a variety of therapies, such as the treatment of Age-related Macular Degeneration (AMD) and myocardial infarct. Once administered to the patient, the MSCs typically migrate (or home) to the damaged tissue and exert their therapeutic effects through paracrine signaling and by promoting survival, repair and regeneration of the neighbouring cells in the damaged tissue.

Current therapies typically involve the infusion of a mixture of MSC subtypes some of which do not migrate efficiently to the tissue of interest. This necessitates the use of a high cell-dose which can lead to off-target side effects and volume-related side effects. MSCs are typically obtained from bone marrow and so it is difficult to obtain large amounts.

SUMMARY OF THE INVENTION

This invention relates to a novel cell type that has not been previously identified or isolated, the immuno-modulatory progenitor cell. This IMP cell is quite distinct and different to both MSCs and MPCs in its composition, function and characteristics which impart an enhanced immuno-modulatory capacity.

The inventors have surprisingly identified a new immuno-modulatory progenitor (IMP) cell having a specific marker expression pattern. In particular, the IMP cell expresses MIC A/B, CD304 (Neuropilin 1), CD178 (FAS ligand), CD289 (Toll-like receptor 9), CD363 (Sphingosine-1-phosphate receptor 1), CD99, CD181 (C—X—C chemokine receptor type 1; CXCR1), epidermal growth factor receptor (EGF-R), CXCR2 and CD126, The IMP cell expresses significantly greater amounts of these markers than a mesencymal stem cell (MSC). The IMP cells of the invention can be isolated from mononuclear cells (MCs), such as peripheral blood MCs. The IMP cells are capable of efficiently migrating to and repairing damaged tissues. In particular, they are capable of homing, adherence, transmigration, proliferation, angiogenic effects and paracrine signalling.

Accordingly, the invention provides an immuno-modulatory progenitor (IMP) cell, wherein the cell expresses detectable levels of MIC A/B, CD304 (Neuropilin 1), CD178 (FAS ligand), CD289 (Toll-like receptor 9), CD363 (Sphingosine-1-phosphate receptor 1), CD99, CD181 (C—X—C chemokine receptor type 1; CXCR1), epidermal growth factor receptor (EGF-R), CXCR2 and CD126.

The invention also provides:
a population of two or more IMP cells of the invention;
a population of immuno-modulatory progenitor (IMP) cells, wherein
  (i) at least 90% of the cells in the population express detectable levels of MIC A/B,
  (ii) at least 60% of the cells in the population express detectable levels of CD304 (Neuropilin 1),
  (iii) at least 45% of the cells in the population express detectable levels of CD178 (FAS ligand),
  (iv) at least 10% of the cells in the population express detectable levels of CD289 (Toll-like receptor 9),
  (v) at least 15% of the population express detectable levels of CD363 (Sphingosine-1-phosphate receptor 1),
  (vi) at least 20% of the cells in the population express detectable levels of CD99,
  (vii) at least 80% of the cells in the population express detectable levels of CD 181 (C—X—C chemokine receptor type 1; CXCR1),
  (viii) at least 30% of the cells in the population express detectable levels of epidermal growth factor receptor (EGF-R),
  (xi) at least 60% of the cells in the population express detectable levels of CXCR2 and
  (x) at least 5% of the cells in the population express detectable levels of CD126;
a pharmaceutical composition comprising (a) an IMP cell of the invention or a population of the invention and (b) a pharmaceutically acceptable carrier or diluent, one or more liposomes and/or one or more microbubbles;
a method of producing a population of IMP cells of the invention, comprising (a) culturing mononuclear cells (MCs) under conditions which induce the MCs to differentiate into IMP cells and (b) harvesting and culturing those IMP cells which have an expression pattern as defined above and thereby producing a population of the invention;
a method of repairing a damaged tissue in a patient, comprising administering to the patient a population of the invention or a pharmaceutical composition of the invention, wherein the population or composition comprises a therapeutically effective number of cells, and thereby treating the damaged tissue in the patient;
a population of the invention or a pharmaceutical composition of the invention for use in a method of repairing a damaged tissue in a patient; and
a population of the invention or a pharmaceutical composition of the invention for use in a method of treating a cardiac, bone, cartilage, tendon, ligament, liver, kidney or lung injury or disease in a patient.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a cell" includes "cells", reference to "a tissue" includes two or more such tissues, reference to "a patient" includes two or more such patients, and the like.

All publications, patents and patent applications cited herein, whether supra or infra, are hereby incorporated by reference in their entirety.

IMP Cell of the Invention

The present invention provides an immuno-modulatory progenitor (IMP) cell. The IMP cell expresses detectable levels of MIC A/B, CD304 (Neuropilin 1), CD178 (FAS ligand), CD289 (Toll-like receptor 9), CD363 (Sphingosine-1-phosphate receptor 1), CD99, CD181 (C—X—C chemokine receptor type 1; CXCR1), epidermal growth factor receptor (EGF-R), CXCR2 and CD126.

MIC allows adaptation of cells and their immuno-behaviour in an inflammatory context by decreasing their susceptibility to NK killing.

CD304 (alternate name Neuropilin 1) is a co-receptor for vascular endothelial growth factor (VEGF) and has roles in angiogenesis, cell survival, migration and invasion.

CD178 (alternate name FAS ligand) maintains cell phenotype and controls differentiation. It is also capable of inducing proliferation of cells. Although FAS ligand is known primarily in apoptotic signalling, it has been shown that FAS and FAS ligand expressing cells are resistant to FAS-induced apoptosis.

CD289 (alternate name Toll-like receptor 9) is involved in the modulation of immune responses and may facilitate cell migration towards a target tissue.

Sustained activation of CD363 (alternate name is Sphingosine-1-phosphate receptor 1) has resulted in increased engraftment of cells in-vivo. CD363 also promotes angiogenesis, modulates cell homing, modulates trafficking and migration of cells and regulates chemotaxis.

CD99 is involved in cell adhesion and transmigration.

There are two classes of interleukin-8 (IL-8) receptors, CXCR1 (or CD181) and CXCR2. Both receptors bind IL-8 with high affinity, in contrast to the other CXC chemokines. Functionally, CXCR1 and CXCR2 have been shown to play significant roles in proliferation, migration, invasion and angiogenesis. Damaged tissues release a variety of soluble inflammatory factors, such as macrophage migration inhibitory factor (MIF) and interleukin-8, and these factors may attract the IMP cells of the invention (and other inflammatory cells) to the damaged tissue though binding to binding CXCR1 and/or CXCR2.

EGF-R is involved in cell migration, adhesion and proliferation.

CD126 (alternate name is IL-6R1) increases immune-privilege

The IMP cells of the invention have numerous advantages. The key advantages will be summarized here. However, further advantages will become apparent from the discussion below.

The IMP cells of the invention may advantageously be used to repair damaged tissues in patients. The IMP cells are capable of efficiently migrating (or homing) to a damaged tissue and exerting anti-inflammatory effects in the tissue. This is discussed in more detail below. One of the most important abilities of the IMP cells is to migrate (or home) to injured sites, which involves chemotaxis. This is based on chemokine-signalling and utilises mechanisms such as rolling, adhesion and transmigration. The anti-inflammatory effects of the IMP cells promote survival, repair and regeneration of the neighbouring cells in the damaged tissue. The cells are also able to exert paracrine effects such as the secretion of angiogenic, chemotactic and anti-apoptotic factors. This is also discussed in more detail below.

As discussed in more detail below, the IMP cells are produced from mononuclear cells (MCs), such as peripheral MCs, taken from an individual, such as a human individual. Since the IMP cells are produced from MCs, they may be produced easily (such as from peripheral blood) and may be autologous for the patient to be treated and thereby avoid the risk of immunological rejection by the patient.

It is possible, in principle, to produce an unlimited number of IMP cells from a single individual, since various samples of MCs (i.e. various samples of blood) may be obtained. It is certainly possible to produce very large numbers of IMP cells from a single individual. The IMP cells of the invention can therefore be made in large numbers.

The IMP cells of the invention are produced in clinically relevant conditions, for instance in the absence of trace amounts of endotoxins and other environmental contaminants, as well as animal products such as fetal calf serum. This makes the IMP cells of the invention particularly suitable for administration to patients.

Since the IMP cells of the invention are produced from MCs, they are substantially homologous and may be autologous. They also avoid donor-to-donor variation, which frequently occurs with MSCs. Numerous populations of IMP cells of the invention can be produced from a single sample taken from the patient before any other therapy, such as chemotherapy or radiotherapy, has begun. Therefore, the IMP cells of the invention can avoid any of the detrimental effects of those treatments.

The IMP cells of the invention can be made quickly. IMP cells can be produced from MCs in less than 30 days, such as in about 22 days.

The production of IMP cells from MCs avoids the moral and ethical implications involved with using mesenchymal stem cells MSCs derived from human embryonic stem cells (hESCs).

The IMP cells of the invention are typically produced from human MCs. The IMP cells of the invention are therefore typically human. Alternatively, the IMP cells may be produced from MCs from other animals or mammals, for instance from commercially farmed animals, such as horses, cattle, sheep or pigs, from laboratory animals, such as mice or rats, or from pets, such as cats, dogs, rabbits or guinea pigs.

The IMP cells of the invention can be identified as immunomodulatory progenitor cells using standard methods known in the art, including expression of lineage restricted markers, structural and functional characteristics. The IMP cells will express detectable levels of cell surface markers known to be characteristic of IMPs. These are discussed below.

The IMP cells of the invention are capable of successfully completing differentiation assays in vitro to confirm that they are of mesodermal lineage. Such assays include, but are not limited to, adipogenic differentiation assays, osteogenic differentiation assays and neurogenic differentiation assays (Zaim M et al Ann Hematol. 2012 August; 91(8):1175-86).

The IMP cells of the invention are not stem cells. In particular, they are not MSCs. They are terminally differentiated. Although they can be forced under the right conditions in vitro to differentiating, for instance into cartilage or bone cells, they typically do not differentiate in vivo. The IMP cells of the invention have their effects by migrating to the damaged tissue and exerting paracrine signalling in the damaged tissue. In particular, the IMP cells are preferably capable of inducing anti-flammatory effects in the damaged tissue. This is discussed in more detail below.

The IMP cells of the invention are typically characterised by a spindle-shaped morphology. The IMP cells are typically fibroblast-like, i.e. they have a small cell body with a few cell processes that are long and thin. The cells are typically from about 10 to about 20 μm in diameter.

The IMP cells of the invention are distinguished from known cells, including MSCs, via their marker expression pattern. The IMPs express detectable levels of MIC A/B, CD304 (Neuropilin 1), CD178 (FAS ligand), CD289 (Toll-like receptor 9), CD363 (Sphingosine-1-phosphate receptor 1), CD99, CD181 (C—X—C chemokine receptor type 1; CXCR1), epidermal growth factor receptor (EGF-R), CXCR2 and CD126. The IMPs preferably express an increased amount of these markers compared with MSCs. This can be determined by comparing the expression level/amount of the markers in an IMP of the invention with the expression level/amount in an MSC using the same technique under the same conditions. Suitable MSCs are commercially available. The MSC used for comparison is preferably a human MSC. Human MSCs are commercially available from Mesoblast® Ltd, Osiris Therapeutics® Inc. or Lonza®. The human MSC is preferably obtained from Lonza®. Such cells were used for the comparison in the Example. The MSC may be derived from any of the animals or mammals discussed above.

The IMP cells preferably express an increased amount of one or more of MIC A/B, CD304 (Neuropilin 1), CD178 (FAS ligand), CD289 (Toll-like receptor 9), CD363 (Sphingosine-1-phosphate receptor 1), CD99, CD181 (C—X—C chemokine receptor type 1; CXCR1), epidermal growth factor receptor (EGF-R), CXCR2 and CD126 compared with a MSC. The IMP cells preferably express an increased amount of all of the ten markers compared with a MSC.

Standard methods known in the art may be used to determine the detectable expression or increased expression of various markers discussed above (and below). Suitable methods include, but are not limited to, immunocytochemistry, immunoassays, flow cytometry, such as fluorescence activated cells sorting (FACS), and polymerase chain reaction (PCR), such as reverse transcription PCR (RT-PCR). Suitable immunoassays include, but are not limited to, Western blotting, enzyme-linked immunoassays (ELISA), enzyme-linked immunosorbent spot assays (ELISPOT assays), enzyme multiplied immunoassay techniques, radio-allergosorbent (RAST) tests, radioimmunoassays, radiobinding assays and immunofluorescence. Western blotting, ELISAs and RT-PCR are all quantitative and so can be used to measure the level of expression of the various markers if present. The use of high-throughput FACS (HT-FACS) is disclosed in the Example. The expression or increased expression of any of the markers disclosed herein is preferably done using HT-FACS. Antibodies and fluorescently-labelled antibodies for all of the various markers discussed herein are commercially-available.

The IMP cells of the invention preferably demonstrate an antibody mean fluorescence intensity (MFI) of at least 330, such as at least 350 or at least 400, for MIC A/B, an MFI of at least 210, such as at least 250 or at least 300, for CD304 (Neuropilin 1), an MFI of at least 221, such as at least 250 or at least 300, for CD178 (FAS ligand), an MFI of at least 186, such as at least 200 or at least 250, for CD289 (Toll-like receptor 9), an MFI of at least 181, such as at least 200 or at least 250, for CD363 (Sphingosine-1-phosphate receptor 1), an MFI of at least 184, such as at least 200 or at least 250, for CD99, an MFI of at least 300, such as at least 350 or at least 400, for CD181 (C—X—C chemokine receptor type 1; CXCR1), an MFI of at least 173, such as at least 200 or at least 250, for epidermal growth factor receptor (EGF-R), an MFI of at least 236, such as at least 250 or at least 300, for CXCR2 and an MFI of at least 160, such as at least 200 or at least 250, for CD126. Mean fluorescent intensity (MFI) is a measure of intensity, time average energy flux measured in watts per square metre. It is an SI unit. The MFI for each marker is typically measured using HT-FACS. The MFI for each marker is preferably measured using HT-FACS as described in the Example.

In addition to the ten markers specified above, the IMP cells of the invention typically express detectable levels of one or more of the other markers shown in Table 1 in the Example. The IMP cells may express detectable levels of any number and combination of those markers.

The IMP cells preferably express detectable levels of one or more of CD267, CD47, CD51/CD61, CD49f, CD49d, CD146, CD340, Notch2, CD49b, CD63, CD58, CD44, CD49c, CD105, CD166, HLA-ABC, CD13, CD29, CD49e, CD73, CD81, CD90, CD98, CD147, CD151 and CD276. The IMP cells more preferably express detectable levels of one or more of CD10, CD111, CD267, CD47, CD273, CD51/CD61, CD49f, CD49d, CD146, CD55, CD340, CD91, Notch2, CD175s, CD82, CD49b, CD95, CD63, CD245, CD58, CD108, B2-microglobulin, CD155, CD298, CD44, CD49c, CD105, CD166, CD230, HLA-ABC, CD13, CD29, CD49e, CD59, CD73, CD81, CD90, CD98, CD147, CD151 and CD276. The IMP cells may express detectable levels of any number and combination of these markers. The IMP cells preferably express detectable levels of all of these markers.

The IMP cells preferably express detectable levels of one or more of CD156b, CD61, CD202b, CD130, CD148, CD288, CD337, SSEA-4, CD349 and CD140b. The IMP cells more preferably express detectable levels of one or more of CD156b, CD61, CD202b, CD130, CD148, CD288, CD337, SSEA-4, CD349, CD140b, CD10, CD111, CD267, CD47, CD273, CD51/CD61, CD49f, CD49d, CD146, CD55, CD340, CD91, Notch2, CD175s, CD82, CD49b, CD95, CD63, CD245, CD58, CD108, B2-microglobulin, CD155, CD298, CD44, CD49c, CD105, CD166, CD230, HLA-ABC, CD13, CD29, CD49e, CD59, CD73, CD81, CD90, CD98, CD147, CD151 and CD276. The IMP cells may express detectable levels of any number and combination of these markers. The IMP cells preferably express detectable levels of all of these markers.

The IMP cells preferably express detectable levels of one or more of CD72, CD133, CD192, CD207, CD144, CD41b, FMC7, CD75, CD3e, CD37, CD158a, CD172b, CD282, CD100, CD94, CD39, CD66b, CD158b, CD40, CD35, CD15, PAC-1, CLIP, CD48, CD278, CD5, CD103, CD209, CD3, CD197, HLA-DM, CD20, CD74, CD87, CD129, CDw329, CD57, CD163, TPBG, CD206, CD243 (BD), CD19, CD8, CD52, CD184, CD107b, CD138, CD7, CD50, HLA-DR, CD158e2, CD64, DCIR, CD45, CLA, CD38, CD45RB, CD34, CD101, CD2, CD41a, CD69, CD136, CD62P, TCR alpha beta, CD16b, CD1a, ITGB7, CD154, CD70, CDw218a, CD137, CD43, CD27, CD62L, CD30, CD36, CD150, CD66, CD212, CD177, CD142, CD167, CD352, CD42a, CD336, CD244, CD23, CD45RO, CD229, CD200, CD22, CDH6, CD28, CD18, CD21, CD335, CD131, CD32, CD157, CD165, CD107a, CD1b, CD332, CD180, CD65 and CD24. The IMP cells may express detectable levels of any number and combination of these markers. The IMP cells preferably express detectable levels of all of these markers.

The IMP cells of the invention are preferably capable of migrating to a specific, damaged tissue in a patient. In other words, when the cells are administered to a patient having a damaged tissue, the cells are capable of migrating (or homing) to the damaged tissue. This is advantageous because it means that the cells can be infused via standard routes, for instance intravenously, and will then target the site of damage. The cells do not have to be delivered to the damaged tissue. The damage may be due to injury or disease as discussed in more detail below.

The specific tissue is preferably cardiac, bone, cartilage, tendon, ligament, liver, kidney or lung tissue. This applies not only to migration, but also adherence, transmigration, proliferation, anti-inflammatory effects and angiogenesis as discussed in more detail below.

The ability of the IMP cells of the invention to migrate to damaged tissue may be measured using standard assays known in the art. Suitable methods include, but are not limited to, genomic reverse transcription polymerase chain reaction (RT-PCR with or without reporter genes) and labelling techniques.

RT-PCR is the most straightforward and simple means to trace the IMP cells of the invention within a patient. A transduced transgene or individual donor markers can be used for this purpose and transplanted cell-specific signals have been obtained in several patient studies. The results are generally semi-quantitative.

Alternatively, the IMP cells of the invention may be stained with a dye of interest, such as a fluorescent dye, and may be monitored in the patient via the signal from the dye. Such methods are routine in the art.

Migration (or homing) is typically determined by measuring the number of cells that arrive at the damaged tissue. It may also be measured indirectly by observing the numbers of cells that have accumulated in the lungs (rather than the damaged tissue).

Damaged heart tissue releases inflammatory chemokines and cytokines, such as stromal cell-derived factor-1 (SDF-1), interleukin-8 (IL-8), tumor necrosis factor-alpha (TNF-alpha), granulocyte-colony-stimulating factor (G-CSF), vascular endothelial growth factor (VEGF) and hepatocyte growth factor (HGF). In addition, myocardial infarct increases the levels of VEGF and erythropoietin (EPO). CXCR4 binds to its ligand SDF-1 and so IMP cells of the invention expressing CXCR4 will migrate towards the gradient of SDF-1 generated by the damaged heart tissue. Other damaged tissues, such as bone, also release SDF-1. If the specific, damaged tissue is cardiac tissue, the IMP cells of the invention preferably express detectable levels of CXCR4 or express an increased amount of CXCR4 compared with MSCs.

If the specific, damaged tissue is bone tissue, the IMP cells of the invention preferably express detectable levels of TGF-beta 3, bone morphogenetic protein-6 (BMP-6), SOX-9, Collagen-2, CD117 (c-kit), chemokine (C—C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Ra, PDGF-R$\beta$3, CXCR4, C—C chemokine receptor type 1 (CCR1), IGF-1 receptor (IGF-1R), hepatocyte growth factor receptor (HGFR), CXCL12 and NFkappaB. The bone-homing IMP cells of the invention preferably express an increased amount of one or more of, or even all of, these factors compared with mesenchymal stem cells MSCs. The detectable expression of these markers may be measured as discussed above.

The IMP cells of the invention are preferably capable of adhering to a specific, damaged tissue in a patient. Adherence and adhesion assay are known in the art (Humphries, Methods Mol Biol. 2009; 522:203-10).

The IMP cells of the invention are preferably capable of transmigrating through the vascular endothelium to a specific, damaged tissue in a patient. Transmigration assays are known in the art (Muller and Luscinskas, Methods Enzymol. 2008; 443: 155-176).

The IMP cells of the invention are preferably capable of proliferating in a specific, damaged tissue in a patient. Cell proliferation assays are well known in the art. Such assays are commercially available, for instance from Life Technologies®.

The IMP cells of the invention are preferably capable of promoting angiogenesis in a specific, damaged tissue in a patient. Angiogenesis assays are known in the art (Auerback et al., Clin Chem. 2003 January; 49(1):32-40).

The IMP cells of the invention are preferably capable of having anti-inflammatory effects in a damaged tissue of a patient. The ability of the IMP cells of the invention to have anti-inflammatory effects may also be measured using standard assays known in the art. Suitable methods include, but are to not limited to, enzyme-linked immunosorbent assays (ELISAs) for the secretion of cytokines, enhanced mixed leukocyte reactions and up-regulation of co-stimulatory molecules and maturation markers, measured by flow cytometry. Specific methods that may be used are disclosed in the Example. The cytokines measured are typically interleukins, such as interleukin-8 (IL-8), selectins, adhesion molecules, such as Intercellular Adhesion Molecule-1 (ICAM-1), and chemoattractant proteins, such as monocyte chemotactic protein-1 (MCP-1) and tumour necrosis factor alpha (TNF-alpha). Assays for these cytokines are commercially-available. Anti-inflammatory factors are preferably detected and measured using the Luminex® assay described in the Examples. Such assays are commercially available from Life Technologies®.

The IMP cells preferably secrete detectable levels of one or more of interleukin-6 (IL-6), IL-8, C—X—C motif chemokine 10 (CXCL10; interferon gamma-induced protein 10; IP-10), Chemokine (C—C motif) ligand 2 (CCL2; monocyte chemotactic protein-1; MCP-1) and Chemokine (C—C motif) ligand 5 (CCL5; regulated on activation, normal T cell expressed and secreted; RANTES). The IMP cells may secrete any number and combination of these factors. The IMP cells preferably secrete all of these markers.

The IMP cells preferably secrete an increased amount of one or more of IL-6, IL-8, IP-10, MCP-1 and RANTES compared with a MSC. The IMP cells may secrete an increased amount of any number and combination of these factors. The IMP cells preferably secrete an increased amount of all of these markers.

The IMP cells preferably secrete a decreased amount of interleukin-10 (IL-10) and/or IL-12 compared with a mesenchymal stem cell MSC. IL-10 and IL-12 are pro-inflammatory cytokines.

The IMP cells of the invention are more preferably capable of migrating to a damaged tissue in a patient and having anti-inflammatory effects in the damaged tissue. This allows the damage to be repaired effectively and reduces the number of cells that need to be administered.

The IMP cells of the invention will express a variety of different other markers over and above those discussed above. Some of these will assist the IMP cells will their ability to migrate to a damaged tissue and have anti-inflammatory effects once there. Any of the IMP cells of the invention may further express detectable levels of one or more of (i) insulin-like growth factor-1 (IGF-1), (ii) IGF-1 receptor; (iii) C—C chemokine receptor type 1 (CCR1), (iv) stromal cell-derived factor-1 (SDF-1), (v) hypoxia-inducible factor-1 alpha (HIF-1 alpha), (vi) Akt1 and (vii) hepatocyte growth factor (HGF) and/or granulocyte colony-stimulating factor (G-CSF).

IGF-1 receptors promote migration capacity towards an IGF-1 gradient. One of the mechanisms by which IGF-1 increases migration is by up-regulating CXCR4 on the surface of the to cells, which makes them more sensitive to SDF-1 signaling. This is discussed above.

CCR1 is the receptor for CCL7 (previously known as MCP3) increases homing and engraftment capacity of MSCs (and so would be expected to have the same effect for the IMP cells of the invention) and can increase the capillary density in injured myocardium through paracrine signalling.

HIF-1 alpha activates pathways that increase oxygen delivery and promote adaptive pro-survival responses. Among the many target genes of HIF-1 alpha are erythropoietin (EPO), endothelin and VEGF (with its receptor Flk-1). IMP cells that express or express an increased amount of HIF-1alpha will have upregulated expression of paracrine stimuli of for example several vasculogenic growth factors that may promote a more therapeutic subtype. As described in more detail below, the IMP cells of the invention can be preconditioned into a more therapeutic subtype by culturing them under hypoxic conditions (less than 20% oxygen), such as for example about 2% or about 0% oxygen.

Akt1 is an intracellular serine/threonine protein kinase that plays a key role in multiple cellular processes such as glucose metabolism, cell proliferation, apoptosis, transcription and cell migration. Overexpression of Akt1 has been shown to prevent rat MSCs from undergoing apoptosis and will have the same effect in the IMP cells of the invention. Protection from apoptosis will enhance the therapeutic effect of the IMP cells.

The overexpression of HGF by MSCs has been shown to prevent post-ischemic heart failure by inhibition of apoptosis via calcineurin-mediated pathway and angiogenesis. HGF and G-CSF exhibit synergistic effects in this regard. MSCs that have a high expression of HGF and its receptor c-met also have an increased migratory capacity into the damaged tissue, achieved through hormonal, paracrine and autocrine signaling. The same will be true for the IMP cells of the invention expressing HGF and/or G-CSF.

The IMP cells may express detectable levels off one or more of (i) to (vii) defined above. The IMP cells of the invention preferably express an increased amount of one or more of (i) to (vii) compared with MSCs. Quantitative assays for cell markers are described above. The detectable expression of these markers and their level of expression may be measured as discussed above.

Any of the IMP cells of the invention may express detectable levels of one or more of (i) vascular endothelial growth factor (VEGF), (ii) transforming growth factor beta (TGF-beta), (iii) insulin-like growth factor-1 (IGF-1), (iv) fibroblast growth factor (FGF), (v) tumour necrosis factor alpha (TNF-alpha), (vi) interferon gamma (IFN-gamma) and (vii) interleukin-1 alpha (IL-1 alpha). Conditioned medium from cells overexpressing VEGF has been shown to alleviate heart failure in a hamster model. Hence, the IMP cells of the invention which express or express an increased amount of VEGF will have the same effect of damaged cardiac tissue.

The IMP cells may express detectable levels of one or more of (i) to (vii). The IMP cells of the invention may express an increased amount of one or more of (i) to (vii) compared with MSCs. Quantitative assays for cell markers are described above. The detectable expression of these markers and their level of expression may be measured as discussed above.

In both sets of definitions of (i) to (vii) given above, any combination of one or more of (i) to (vii) may be expressed or expressed in an increased amount. For instance, for each definition of (i) to (vii), the IMP cells may express detectable levels of, or express an increased amount of, (i); (ii); (iii); (iv); (v); (vi); (vii); (i) and (ii); (i) and (iii); (i) and (iv); (i) and (v); (i) and (vi); (i) and (vii); (ii) and (iii); (ii) and (iv); (ii) and (v); (ii) and (vi); (ii) and (vii); (iii) and (iv); (iii) and (v); (iii) and (vi); (iii) and (vii); (iv) and (v); (iv) and (vi); (iv) and (vii); (v) and (vi); (v) and (vii); (vi) and (vii); (i), (ii) and (iii); (i), (ii) and (iv); (i), (ii) and (v); (i), (ii) and (vi); (i), (ii) and (vii); (i,), (iii) and (iv); (i), (iii) and (v); (i), (iii) and (vi); (i), (iii) and (vii); (i), (iv) and (v); (i), (iv) and (vi); (i), (iv) and (vii); (i), (v) and (vi); (i), (v) and (vii); (i), (vi) and (vii); (ii), (iii) and (iv); (ii), (iii) and (v); (ii), (iii) and (vi); (ii), (iii) and (vii); (ii), (iv) and (v); (ii), (iv) and (vi); (ii), (iv) and (vii); (ii), (v) and (vi); (ii), (v) and (vii); (ii), (vi) and (vii); (iii), (iv) and (v); (iii), (iv) and (vi); (iii), (iv) and (vii); (iii), (v) and (vi); (iii), (v) and (vii); (iii), (vi) and (vii); (iv), (v) and (vi); (iv), (v) and (vii); (iv), (vi) and (vii); (v), (vi) and (vii); (i), (ii), (iii) and (iv); (i), (ii), (iii) and (v); (i), (ii), (iii) and (vi); (i), (ii), (iii) and (vii); (i), (ii), (iv) and (v); (i), (ii), (iv) and (vi); (i), (ii), (iv) and (vii); (i), (ii), (v) and (vi); (i), (ii), (v) and (vii); (i), (ii), (vi) and (vii); (i), (iii), (iv) and (v); (i), (iii), (iv) and (vi); (i), (iii), (iv) and (vii); (i), (iii), (v) and (vi); (i), (iii), (v) and (vii); (i), (iii), (vi) and (vii); (i), (iv), (v) and (vi); (i), (iv), (v) and (vii); (i), (iv), (vi) and (vii); (i), (v), (vi) and (vii); (ii), (iii), (iv) and (v); (ii), (iii), (iv) and (vi); (ii), (iii), (iv) and (vii); (ii), (iii), (v) and (vi); (ii), (iii), (v) and (vii); (ii), (iii), (vi) and (vii); (ii), (iv), (v) and (vi); (ii), (iv), (v) and (vii); (ii), (iv), (vi) and (vii); (ii), (v), (vi) and (vii); (iii), (iv), (v) and (vi); (iii), (iv), (v) and (vii); (iii), (iv), (vi) and (vii); (iii), (v), (vi) and (vii); (iv), (v), (vi) and (vii); (i), (ii), (iii), (iv) and (v); (i), (ii), (iii), (iv) and (vi); (i), (ii), (iii), (iv) and (vii); (i), (ii), (iii), (v) and (vi); (i), (ii), (iii), (v) and (vii); (i), (ii), (iii), (vi) and (vii); (i), (ii), (iv), (v) and (vi); (i), (ii), (iv), (v) and (vii); (i), (ii), (iv), (vi) and (vii); (i), (ii), (v), (vi) and (vii); (i), (iii), (iv), (v) and (vi); (i), (iii), (iv), (v) and (vii); (i), (iii), (iv), (vi) and vii); (i), (iii), (v), (vi) and (vii); (i), (iv), (v), (vi) and (vii); (ii), (iii), (iv), (v) and (vi); (ii), (iii), (iv), (vi) and (vii); (ii), (iii), (v), (vi) and (vii); (ii), (iv), (v), (vi) and (vii); (iii), (iv), (v), (vi) and vii); (i), (ii), (iii), (iv), (v) and (vi); (i), (ii), (iii), (iv), (v) and (vii); (i), (ii), (iii), (iv), (vi) and (vii); (i), (ii), (iii), (v), (vi) and (vii); (i), (ii), (iv), (v), (vi) and (vii); (i), (iii), (iv), (v), (vi) and (vii); (ii), (iii), (iv), (v), (vi) and (vii); or (i), (ii), (iii), (iv), (v), (vi) and (vii). The combinations for each definition of (i) to (vii) are independently selectable from this list.

In addition to any of the markers discussed above, the IMP cells of the invention preferably also express detectable levels of, LIF and/or platelet-derived growth factor (PDGF) receptors. The IMP cells of the invention preferably express an increased amount of LIF and/or platelet-derived growth factor (PDGF) receptors compared with mesenchymal stem cells. The PDGF receptors are preferably PDGF-A receptors and/or PSDGF-B receptors. MSCs that have high expression of these receptors can migrate effectively into areas in which platelets have been activated, such as wounds and thrombotic vessels. The same will be true of IMP cells expressing or expressing an increased amount of the receptors.

The IMP cells of the invention are preferably autologous. In other words, the cells are preferably derived from the patient into which the cells will be administered. Alternatively, the IMP cells are preferably allogeneic. In other words, the cells are preferably derived from a patient that is immunologically compatible with the patient into which the cells will be administered. An IMP cell of the invention may be isolated, substantially isolated, purified or substantially purified. The IMP cell is isolated or purified if it is completely free of any other components, such as culture medium, other cells of the invention or other cell types. The IMP cell is substantially isolated if it is mixed with carriers or diluents, such as culture medium, which will not interfere with its intended use. Alternatively, the IMP cell of the invention may be present in a growth matrix or immobilized on a surface as discussed below.

IMP cells of the invention may be isolated using a variety of techniques including antibody-based techniques. Cells may be isolated using negative and positive selection techniques based on the binding of monoclonal antibodies to those surface markers which are present on the IMP cell (see above). Hence, the IMP cells may be separated using any antibody-based technique, including fluorescent activated cell sorting (FACS) and magnetic bead separation.

As discussed in more detail below, the IMP cells may be treated ex vivo. Thus the cells may be loaded or transfected with a therapeutic or diagnostic agent and then used therapeutically in the methods of the invention.

Population of the Invention

The invention also provides a population of two or more IMP cells of the invention. Any number of cells may be present in the population. The population of the invention preferably comprises at least about $5\times10^5$ IMP cells of the invention. The population more preferably comprises at least about $1\times10^6$, at least about $2\times10^6$, at least about 2.5 $2\times10^6$, at least about $5\times10^6$, at least about $1\times10^7$, at least about $2\times10^7$, at least about $5\times10^7$, at least about $1\times10^8$ or at least about $2\times10^8$ IMP cells of the invention. In some instances, the population may comprise at least about $1.0\times 10^7$, at least about $1.0\times10^8$, at least about $1.0\times10^9$, at least about $1.0\times10^{10}$, at least about $1.0\times10^{11}$ or at about least $1.0\times10^{12}$ IMP cells of the invention or even more.

The population comprising two or more IMP cells of the invention may comprise other cells in addition to the IMP cells of the invention. However, at least 70% of the cells in the population are preferably IMP cells of the invention. More preferably, at least about 75%, at least about 80%, at least about 85%, at least about 90%, at least about 97%, at least about 98% or at least about 99% of the cells in the population are IMP cells of the invention.

The invention also provides specific populations of IMP cells. The invention provides a population of immunomodulatory progenitor (IMP) cells, wherein (i) at least 90%, preferably at least 97% and more preferably at least 97.1%, of the cells in the population express detectable levels of MIC A/B, (ii) at least 60%, preferably at least 65% and more preferably at least 65.2%, of the cells in the population express detectable levels of CD304 (Neuropilin 1), (iii) at least 45%, preferably at least 51% and more preferably at least 51.6%, of the cells in the population express detectable levels of CD178 (FAS ligand), (iv) at least 10%, preferably at least 11% and more preferably at least 11.3%, of the cells in the population express detectable levels of CD289 (Toll-like receptor 9), (v) at least 15%, preferably at least 18% and more preferably at least 18.7%, of the population express detectable levels of CD363 (Sphingosine-1-phosphate receptor 1), (vi) at least 20%, preferably at least 24% and more preferably at least 24.8%, of the cells in the population express detectable levels of CD99, (vii) at least 80%, preferably at least 85%, of the cells in the population express detectable levels of CD181 (C—X—C chemokine receptor type 1; CXCR1), (viii) at least 30%, preferably at least 33% and more preferably at least 33.3%, of the cells in the population express detectable levels of epidermal growth factor receptor (EGF-R), (xi) at least 60%, preferably at least 68% and more preferably at least 68.8%, of the cells in the population express detectable levels of CXCR2 and (x) at least 5%, preferably at least 7% and more preferably at least 7.05%, of the cells in the population express detectable levels of CD126.

The cells in these preferred populations may further express detectable levels of any of the markers discussed above with reference to the IMP of the invention. The cells in the these preferred populations may have any of the advantageous properties of the IMP cells discussed above.

At least 90%, such as at least 95%, of the cells in the population preferably express detectable levels of one or more of CD10, CD111, CD267, CD47, CD273, CD51/CD61, CD49f, CD49d, CD146, CD55, CD340, CD91, Notch2, CD175s, CD82, CD49b, CD95, CD63, CD245, CD58, CD108, B2-microglobulin, CD155, CD298, CD44, CD49c, CD105, CD166, CD230, HLA-ABC, CD13, CD29, CD49e, CD59, CD73, CD81, CD90, CD98, CD147, CD151 and CD276. At least 90%, such as at least 95%, of the cells in the population may express detectable levels of any number and combination of these markers. At least 90%, such as at least 95%, of the cells in the population preferably express detectable levels of all of these markers.

At least 80%, such as at least 85%, of the cells in the population preferably express detectable levels of one or more of CD156b, CD61, CD202b, CD130, CD148, CD288, CD337, SSEA-4, CD349 and CD140b. At least 80%, such as at least 85%, of the cells in the population may express detectable levels of any number and combination of these markers. At least 80%, such as at least 85%, of the cells in the population preferably express detectable levels of all of these markers.

At least 70%, such as at least 75%, of the cells in the population preferably express detectable levels of one or more of CD318, CD351, CD286, CD46, CD119 and CD132. At least 70%, such as at least 75%, of the cells in the population may express detectable levels of any number and combination of these markers. At least 70%, such as at least 75%, of the cells in the population preferably express detectable levels of all of these markers.

1% or fewer, such as 0.5% or fewer, of the cells in the population preferably express detectable levels of one or more of CD72, CD133, CD192, CD207, CD144, CD41b, FMC7, CD75, CD3e, CD37, CD158a, CD172b, CD282, CD100, CD94, CD39, CD66b, CD158b, CD40, CD35, CD15, PAC-1, CLIP, CD48, CD278, CD5, CD103, CD209, CD3, CD197, HLA-DM, CD20, CD74, CD87, CD129, CDw329, CD57, CD163, TPBG, CD206, CD243 (BD), CD19, CD8, CD52, CD184, CD107b, CD138, CD7, CD50, HLA-DR, CD158e2, CD64, DCIR, CD45, CLA, CD38, CD45RB, CD34, CD101, CD2, CD41a, CD69, CD136, CD62P, TCR alpha beta, CD16b, CD1a, ITGB7, CD154, CD70, CDw218a, CD137, CD43, CD27, CD62L, CD30, CD36, CD150, CD66, CD212, CD177, CD142, CD167, CD352, CD42a, CD336, CD244, CD23, CD45RO, CD229, CD200, CD22, CDH6, CD28, CD18, CD21, CD335, CD131, CD32, CD157, CD165, CD107a, CD1b, CD332, CD180, CD65 and CD24. 1% or fewer, such as 0.5% or fewer, of the cells in the population may express detectable levels of any number and combination of these markers. 1% or fewer, such as 0.5% or fewer, of the cells in the population preferably express detectable levels of all of these markers.

In any of the embodiments above where populations are defined with reference to % of cells expressing certain markers, the populations preferably comprise at least 5,000 cells, such as at least 6,000, at least 7,000, at least 8,000, at least 9,000, at least 10,000, at least 20,000, at least 30,000 or at least 40,000 cells. These populations may comprise any of the number of cells discussed above.

Any of the populations of cells disclosed herein may be diluted with other cells before use. For instance, the population may be combined with patient blood, mononuclear cells (MCs), MSCs, progenitor cells of the mesodermal lineage (PMLs) or a combination thereof. PMLs are disclosed in PCT/GB2012/051600 (published as WO 2013/005053).

The populations of the invention are advantageous for therapy as discussed below. This ability to produce populations comprising large numbers of IMP cells of the invention is one of the key advantages of the invention. The invention allows the treatment of patients with a population of cells of which most, if not all, migrate efficiently to the tissue of interest and have anti-inflammatory effects once there. This allows the use of a low cell-dose and avoids off-target side effects and volume-related side effects.

The population of the invention is preferably homologous. In other words, all of the IMP cells in the population are preferably genotypically and phenotypically identical. The population is preferably autologous or allogeneic as defined above.

However, the population can also be semi-allogeneic. Semi-allogeneic populations are typically produced from mononuclear cells from two or more patients that are immunologically compatible with the patient into which the population will be administered. In other words, all of the cells in the population are preferably genetically identical or sufficiently genetically identical that the population is immunologically compatible with the patient into which the population will be administered. Since the IMP cells of the invention may be derived from a patient, they may be autologous with the patient to be treated (i.e. genetically identical with the patient or sufficiently genetically identical that they are compatible for administration to the patient).

The population of the invention may be isolated, substantially isolated, purified or substantially purified. A population is isolated or purified if it is completely free of any other components, such as culture medium and other cells. A population is substantially isolated if it is mixed with carriers or diluents, such as culture medium, which will not interfere with its intended use. Other carriers and diluents are discussed in more detail below. A substantially isolated or substantially purified population does not comprise cells other than the IMP cells of the invention. In some embodiments, the population of the invention may be present in a growth matrix or immobilized on a surface as discussed below.

The population is typically cultured in vitro. Techniques for culturing cells are well known to a person skilled in the art. The cells are may be cultured under standard conditions of 37° C., 5% $CO_2$ in medium without serum. The cells are preferably cultured under low oxygen conditions as discussed in more detail below. The cells may be cultured in any suitable flask or vessel, including wells of a flat plate such as a standard 6 well plate. Such plates are commercially available from Fisher scientific, VWR suppliers, Nunc, Starstedt or Falcon. The wells typically have a capacity of from about 1ml to about 4 ml.

The flask, vessel or wells within which the population is contained or cultured may be modified to facilitate handling of the IMP cells. For instance, the flask, vessel or wells may be modified to facilitate culture of the cells, for instance by including a growth matrix. The flask, vessel or wells may be modified to allow attachment of the IMP cells or to allow immobilization of the IMP cells onto a surface. One or more surfaces may be coated with extracellular matrix proteins such as laminin or collagen or any other capture molecules that bind to the cells and immobilize or capture them on the surface(s).

The population may be modified ex vivo using any of the techniques described herein. For instance, the population may be transfected or loaded with therapeutic or diagnostics agents. The population may then be used in the methods of treatment discussed in more detail below.

Method of Producing an IMP Cell of the Invention

The invention also provides a method for producing a population of the invention. The method involves culturing mononuclear cells (MCs) under conditions which induce the MCs to differentiate into IMP cells. The method then involves harvesting and culturing the IMP cells which expresses detectable levels of MIC A/B, CD304 (Neuropilin 1), CD178 (FAS ligand), CD289 (Toll-like receptor 9), CD363 (Sphingosine-1-phosphate receptor 1), CD99, CD181 (C—X—C chemokine receptor type 1; CXCR1), epidermal growth factor receptor (EGF-R), CXCR2 and CD126. The harvested cells may express detectable levels of or increased amounts of any of the markers and factors described above with reference to the cells of the invention.

Mononuclear cells (MCs) and methods of isolating them are known in the art. The MCs may be primary MCs isolated from bone marrow. The MCs are preferably peripheral blood MCs (PBMCs), such as lymphocytes, monocytes and/or macrophages. PBMCs can be isolated from blood using a hydrophilic polysaccharide, such as Ficoll®. For instance, PBMCs may be isolated from blood using Ficoll-Paque® (a commercially-available density medium) as disclosed in the Example.

Before they are cultured, the MCs may be exposed to a mesenchymal stem cell enrichment cocktail. The cocktail preferably comprises antibodies that recognise CD3, CD14, CD19, CD38, CD66b (which are present on unwanted cells) and a component of red blood cells. Such a cocktail cross links unwanted cells with red blood cells forming immunorosettes which may be removed from the wanted MCs. A preferred cocktail is RosetteSep®.

Conditions suitable for inducing MCs to differentiate into mesenchymal cells (tissue mainly derived from the mesoderm) are known in the art. For instance, suitable conditions are disclosed in Capelli, C., et al. (Human platelet lysate allows expansion and clinical grade production of mesenchymal stromal cells from small samples of bone marrow aspirates or marrow filter washouts. Bone Marrow Transplantation, 2007. 40: p. 785-791). These conditions may also be used to induce MCs to differentiate into IMP cells in accordance with the invention.

The method preferably comprises culturing MCs with plasma lysate to induce the MCs to differentiate into IMP cells. Platelet lysate refers to the combination of natural growth factors contained in platelets that has been released through lysing those platelets. Lysis can be accomplished through chemical means (i.e. $CaCl_2$), osmotic means (use of distilled $H_2O$) or through freezing/thawing procedures. Platelet lysate can be derived from whole blood as described in U.S. Pat. No. 5,198,357. Platelet lysate is preferably prepared as described in PCT/GB12/052911 (published as WO 2013/076507). The plasma lysate is preferably human plasma lysate. Platelet lysate, PL, has been shown to have a positive influence on wound healing. A therapeutic platelet lysate is a platelet lysate that is suitable for therapy. The platelet lysate of the invention or the platelet lysate used in the pharmaceutical composition of the invention typically comprises one or more of, preferably all of, PDGF, VEGF, FGF, EGF, and TGF as described above. It also typically comprises TEVIP-2. Lysis of platelets can be accomplished through chemical means (i.e. $CaCl_2$), osmotic means (use of distilled $H_2O$), or through freezing/thawing procedures. Platelet lysate for use in the invention can also be derived from whole blood and can be prepared as described in U.S. Pat. No. 5,198,357, which is incorporated by reference herein. Previously, PL has been prepared through freeze-thaw cycles in varying temperatures ranging from −20 to −80 degrees, by rarely using more than 1 cycle. Our data have shown that the number of whole platelets is only moderately affected by a freeze-thaw cycle in −80/+37 degrees. In fact, in a comparison of −20, −80 and liquid nitrogen freezing, only liquid nitrogen was able to achieve 90% lysis whereas −20 and −80 resulted in 80% and 50% lysis, respectively. Notable however is that the experiment above contained 3 freeze-thaw cycles and thus shows that the preparation of PL in current literature using −80 degrees in one freeze-thaw can only achieve about 20% lysis. Liquid nitrogen also holds the advantage of enabling 3 or more freeze-thaw cycles to be performed within an hour, and is thus a highly suitable method for the clinical setting. Furthermore, liquid nitrogen facilitates process standardization as the liquid form of the gas always is −196° C. whereas freezers can differ in temperature over time, especially when there are multiple users who open the door frequently naturally standardization is of particular importance when preparing a product for use in the clinic. The invention provides a method of producing a platelet lysate (PL) comprising subjecting a population of platelets to at least one freeze-thaw cycle, wherein the freeze portion of each cycle is carried out at a temperature lower than or equal to −78° C. The method may involve any number of freeze-thaw cycles, such as 1, 2, 3, 4, 5, 6, 7, 8, 9, 10, 15, 20, 25, 30 or more. The method preferably comprises subjecting the population of platelets to 5 or fewer freeze-thaw cycles, such as 4 or fewer freeze-thaw cycles, 3 or fewer freeze-thaw cycles or 2 or fewer freeze-thaw cycles. The method more preferably comprises subjecting the population of platelets to only one freeze-thaw cycle, only two freeze-thaw cycles, only three freeze-thaw cycles or only four freeze-thaw cycles. The thaw temperature in each cycle may be any temperature that thaws the platelet composition, such from about 5° C. to about 50° C., such as from about 10° C. to about 45° C. or from about 20° C. to about 40° C. The thaw temperature in each cycle is typically about 37° C. The freeze temperature in each cycle is preferably lower than or equal to about −79° C., lower than or equal to about −80° C., lower than or equal to about −81° C., lower than or equal to about −82° C., lower than or equal to about −83° C., lower than or equal to about −84° C., lower than or equal to about −85° C., lower than or equal to about −86° C., lower than or equal to about −87° C., lower than or equal to about −88° C., lower than or equal to about −89° C., lower than or equal to about −90° C., lower than or equal to about −100° C., lower than or equal to about −110° C., lower than or equal to about −120° C., lower than or equal to about −130° C., lower than or equal to about −140° C., lower than or equal to about −150° C., lower than or equal to about −160° C., lower than or equal to about −170° C., lower than or equal to about −180° C., lower than or equal to about −190° C. or about −196° C. The freeze and thaw temperatures in different cycles of the same method are typically the same. In a preferred embodiment, liquid nitrogen is used as a cryogenic means in each freeze cycle. Immersion in liquid nitrogen in the freeze portion of each cycle typically results in 95% or more lysis of platelets resulting in greater growth factor release and improved function in cell growth, repair and regeneration measurable by, but not limited to, fibroblast and PGDF assay. The invention also provides a platelet lysate produced using a method of the invention. This platelet lysate differs from known lysate because it results from greater than about 80% lysis of the platelets, such as greater than about 85% or greater than about 329.1 90% lysis of the platelets. It therefore comprises more growth factors and an improved function in cell growth, repair and regeneration measurable by, but not limited to, fibroblast and PGDF assay. The platelet lysate is present in the pharmaceutical composition of the invention at a concentration within the range of from about 0.1 [ig to about 1,000 [ig per gram of composition, such as from about 0.2 [ig to about 750 [ig per gram of composition, from about 0.5 [ig to about 500 [ig per gram of composition, from about 1 μg to about 250 [ig per gram of composition, from about 2 μg to about 200 [ig per gram of composition or from about 10 [ig to about 100 [ig per gram of composition. The platelet lysate of the invention or the platelet lysate used in the pharmaceutical composition of the invention may be derived from the platelets of any mammal. The mammal is preferably a human. However, it may be non-human. Suitable non-human animals include, but are not limited to, primates, such as marmosets or monkeys, commercially farmed animals, such as horses, cows, sheeps, goats, alpacas, guanacos, deer or pigs, pets, such as dogs, cats, mice, rats, guinea pigs, ferrets, gerbils or hamsters or wild animals such as badgers or deer.

In a preferred embodiment, step (a) of the method of the invention comprises culturing MCs in a medium comprising platelet lysate for sufficient time to induce the MCs to differentiate into IMP cells. The sufficient time is typically from about 15 to about 25 days, preferably about 22 days. The medium preferably comprises about 20% or less platelet lysate by volume, such as about 15% or less by volume or about 10% or less by volume. The medium preferably comprises from about 5% to about 20% of platelet lysate by volume, such as from about 10% to about 15% by volume. The medium preferably comprises about 10% of platelet lysate by volume.

In another preferred embodiment, step (a) of the method of the invention comprises exposing MCs to a mesenchymal enrichment cocktail and then culturing the MCs in a medium comprising platelet lysate for sufficient time to induce the MCs to differentiate into IMP cells. The sufficient time is typically from about 15 to about 25 days, preferably about 22 days.

In step (a), the medium is preferably Minimum Essential Medium (MEM). MEM is commercially available from various sources including Sigma-Aldrich. The medium preferably further comprises one or more of heparin, L-glutamine and penicillin/streptavidin (P/S). The L-glutamine may be replaced with GlutaMAX® (which is commercially-available from Life Technologies).

As discussed above, some of the IMP cells of the invention express detectable levels of CXCR4. Expression of CXCR4 is cytokine-dependent and is increased when cells are exposed to stem cell factor (SCF), interleukin-6 (IL-6), Flt-3 ligand, hepatocyte growth factor (HGF) and IL-3. The medium may comprise one or more of (i) SCF, (ii) IL-6, (iii) Flt-3 ligand, (iv) hepatocyte growth factor and (v) IL-3, such as (i); (ii); (iii); (iv); (v); (i) and (ii); (i) and (iii); (i) and (iv); (i) and (v); (ii) and (iii); (ii) and (iv); (ii) and (v); (iii) and (iv); (iii) and (v); (iv) and (v); (i), (ii) and (iii); (i), (ii) and (iv); (i), (ii) and (v); (i), (iii) and (iv); (i), (iii) and (v); (i), (iv) and (v); (ii), (iii) and (iv); (ii), (iii) and (v); (ii), (iv) and (v); (iii), (iv) and (v); or (i), (ii), (iii), (iv) and (v). Any of (i) to (v) may be present at from about from about 10 to about about 150 ng/ml.

Step (a) preferably comprises culturing the MCs under conditions which allow the IMP cells to adhere. Suitable conditions are discussed in more detail above.

In step (a), the MCs are preferably cultured under low oxygen conditions. The MCs are preferably cultured at less than about 20% oxygen ($O_2$), such as less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2% or less than about 1% oxygen ($O_2$). The MCs are preferably cultured at from about 0% to about 19% $O_2$, such as from about 1% to about 15% $O_2$, from about 2% to about 10% $O_2$ or from about 5% to about 8% $O_2$. The MCs are most preferably cultured at about 0% $O_2$. The figures for % oxygen (or % $O_2$) quoted above relate to % by volume of oxygen in the gas supplied to the cells during culture, for instance by the cell incubator. It is possible that some oxygen may leak into the incubator or enter when the door is opened.

In step (a), the MCs are most preferably cultured in the presence of platelet lysate and under low oxygen conditions. This combination mimics the natural conditions in the damaged tissue and so result in healthier and more therapeutically potent cells. Conventional cell culture is performed in 20% or 21% oxygen (approximately the atmospheric content) but there is no place in the human body that has this oxygen level. The epithelial cells in the lungs would "see" this oxygen level, but once the oxygen is dissolved and leaves the lungs, it decreases to around 17%. From there, it decreases even further to about 1-2% in the majority of the tissues, but being as low as 0.1% in avascular tissues such as the cartilage in the joints.

In step (b), the method further comprises harvesting and culturing IMP cells which have the necessary marker expression pattern as discussed above. The IMP cells having the necessary marker expression pattern may be harvested using any antibody-based technique, including fluorescent activated cell sorting (FACS) and magnetic bead separation. FACS is preferred. HT-FACS is more preferred.

Any of the methods for culturing IMP cells disclosed in relation to step (a) equally apply to step (b). In particular, the cells are cultured in step (b) in the presence of platelet lysate and under low oxygen conditions as discussed above in relation to step (a).

As will be clear from the discussion above, the method of the invention is carried out in clinically relevant conditions, i.e. in the absence of trace amounts of endotoxins and other environmental contaminants, such as lipopolysaccharides, lipopeptides and peptidoglycans, etc. This makes the IMP cells of the invention particularly suitable for administration to patients.

The MCs are preferably obtained from a patient or an allogeneic donor. The invention also provides a method for producing a population of the invention that is suitable for administration to a patient, wherein the method comprises culturing MCs obtained from the patient under conditions which induce the MCs to differentiate into IMP cells and (b) harvesting and culturing those progenitor cells which have an expression pattern as defined above and thereby producing a population of the invention that is suitable for administration to the patient. The population will be autologous with the patient and therefore will not be rejected upon implantation. The invention also provides a population of the invention that is suitable for administration to a patient and is produced in this manner.

Alternatively, the invention provides a method for producing a population of the invention that is suitable for administration to a patient, wherein the method comprises culturing MCs obtained from a different patient that is immunologically compatible with the patient into which the cells will be administered under conditions which induce the MCs to differentiate into IMP cells and (b) harvesting and culturing those IMP cells which have an expression pattern as defined above and thereby producing a population of the invention that is suitable for administration to the patient. The population will be allogeneic with the patient and therefore will reduce the chance of rejection upon implantation. The invention also provides a population of the invention that is suitable for administration to a patient and is produced in this manner.

Medicaments, Methods and Therapeutic Use

The IMP cells of the invention may be used in a method of therapy of the human or animal body. Thus the invention provides an IMP cell of the invention or a population of the invention for use in a method of treatment of the human or animal body by therapy. In particular, the invention concerns using the IMP cells of the invention or a population of the invention to repair a damaged tissue in a patient. The invention also concerns using the IMP cells of the invention or a population of the invention to treat a cardiac, bone, cartilage, tendon, ligament, liver, kidney or lung injury or disease in the patient.

The invention provides a method of repairing a damaged tissue in a patient, comprising administering to the patient a population of the invention, wherein the population comprises a therapeutically effective number of cells, and thereby treating the damaged tissue in the patient. The invention also provides a population of the invention for use in repairing a damaged tissue in the patient. The invention also provides use of a population of the invention in the manufacture of a medicament for repairing a damaged tissue in a patient.

The tissue is preferably derived from the mesoderm. The tissue is more preferably cardiac, bone, cartilage, tendon, ligament, liver, kidney or lung tissue.

The damage to the tissue may be caused by injury or disease. The injury or disease is preferably a cardiac, bone, cartilage, tendon, ligament, liver, kidney or lung injury or disease in a patient. The invention therefore provides a method of treating a cardiac, bone, cartilage, tendon, ligament, liver, kidney or lung injury or disease in a patient, comprising administering to the patient a population of the invention, wherein the population comprises a therapeutically effective number of cells, and thereby treating the injury or disease in the patient. The invention also provides a population of the invention for use in treating a cardiac, bone, cartilage, tendon, ligament, liver, kidney or lung injury or disease in a patient. The invention also provides use of a population of the invention in the manufacture of a medicament for treating a cardiac, bone, cartilage, tendon, ligament, liver, kidney or lung injury or disease in a patient.

The cardiac injury or disease is preferably selected from myocardial infarct (MI), left ventricular hypertrophy, right ventricular hypertrophy, emboli, heart failure, congenital heart deficit, heart valve disease, arrhythmia and myocarditis.

MI increases the levels of VEGF and EPO released by the myocardium. Furthermore, MI is associated with an inflammatory reaction and infarcted tissue also releases macrophage migration inhibitory factor (MIF), interleukin (IL-6) and KC/Gro-alpha. CCL7 (previously known as MCP3), CXCL1, CXCL2 are significantly upregulated in the heart following myocardial infarct (MI) and might be implicated in regulating engraftment and homing of MSCs to infarcted myocardium.

In a myocardial infarct mice model, IL-8 was shown to highly up-regulate gene expression primarily in the first 2 days post-MI. Remarkably, the increased IL-8 expression was located predominantly in the infarcted area and the border zone, and only to a far lesser degree in the spared myocardium. By activating CXCR2, MIF displays chemokine-like functions and acts as a major regulator of inflammatory cell recruitment and atherogenesis.

The bone disease or injury is preferably selected from fracture, Salter-Harris fracture, greenstick fracture, bone spur, craniosynostosis, Coffin-Lowry syndrome, fibrodysplasia ossificans progressive, fibrous dysplasia, Fong Disease (or Nail-patella syndrome), hypophosphatasia, Klippel-Feil syndrome, Metabolic Bone Disease, Nail-patella syndrome, osteoarthritis, osteitis deformans (or Paget's disease of bone), osteitis fibrosa cystica (or Osteitis fibrosa or Von Recklinghausen's disease of bone), osteitis pubis, condensing osteitis (or osteitis condensans), osteitis condensans osteochondritis dissecans, osteogenesis imperfecta, osteomalacia, osteomyelitis, osteopenia, osteopetrosis, osteoporosis, osteonecrosis, porotic hyperostosis, primary hyperparathyroidism, renal osteodystrophy, bone cancer, a bone lesion associated with metastatic cancer, Gorham Stout disease, primary hyperparathyroidism, periodontal disease, and aseptic loosening of joint replacements. The bone cancer can be Ewing sarcoma, multiple myeloma, osteosarcoma (giant tumour of the bone), osteochondroma or osteoclastoma. The metastatic cancer that results in a bone lesion can be breast cancer, prostate cancer, kidney cancer, lung cancer and/or adult T-cell leukemia.

If the damaged tissue is cardiac tissue or bone tissue, the IMP cells in the population preferably express detectable levels of CD29, CD44, CD73, CD90, CD105, CD271, CXCR1, CXCR2 and CXCR4 and do not express detectable levels of CD14, CD34 and CD45. If the damaged tissue is bone tissue, the IMP cells in the population more preferably express detectable levels of CD29, CD44, CD73, CD90, CD105, CD271, TGF-beta 3, bone morphogenetic protein-6 (BMP-6), SOX-9, Collagen-2, CD117 (c-kit), chemokine (C—C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Rα, PDGF-Rβ, CXCR4, C—C chemokine receptor type 1 (CCR1), IGF-1 receptor (IGF-1R), hepatocyte growth factor receptor (HGFR), CXCL12 and NFkappaB and do not express detectable levels of CD14, CD34 and CD45.

The disease or disorder may be periodontal disease, endometriosis or meniscal tears.

In all instances, the IMP cells of the invention are preferably derived from the patient or an allogeneic donor. Deriving the IMP cells of the invention from the patient should ensure that the IMP cells are themselves not rejected by the patient's immune system. Any difference between the donor and recipient will ultimately cause clearance of the IMP cells, but not before they have repaired at least a part of the damaged tissue.

The invention concerns administering to the patient a therapeutically effective number of IMP cells of the invention to the patient. A therapeutically effective number is a number which ameliorates one or more symptoms of the damage, disease or injury. A therapeutically effective number is preferably a number which repairs the damaged tissue or treats the disease or injury. Suitable numbers are discussed in more detail below.

The IMP cells of the invention may be administered to any suitable patient. The patient is generally a human patient. The patient may be any of the animals or mammals mentioned above with reference to the source of the IMP cells.

The patient may be an infant, a juvenile or an adult. The patient may be known to have a damaged tissue or is suspected of having a damaged tissue. The patient may be susceptible to, or at risk from, the relevant disease or injury. For instance, the patient may be genetically predisposed to heart failure.

The invention may be used in combination with other means of, and substances for, repairing damaged tissue or providing pain relief. In some cases, the IMP cells of the invention may be administered simultaneously, sequentially or separately with other substances which are intended for repairing the damaged tissue or for providing pain relief. The IMP cells may be used in combination with existing treatments for damaged tissue and may, for example, be simply mixed with such treatments. Thus the invention may be used to increase the efficacy of existing treatments of damaged tissue.

The invention preferably concerns the use of IMP cells loaded or transfected with a therapeutic and/or diagnostic agent. A therapeutic agent may help to repair the damaged tissue. A diagnostic agent, such as a fluorescent molecule, may help to identify the location of the IMP cells in the patient. The IMP cells may be loaded or transfected using any method known in the art. The loading of IMP cells may be performed in vitro or ex vivo. In each case, the IMP cells may simply be in contact with the agent in culture. Alternatively, the IMP cells may be loaded with an agent using delivery vehicle, such as liposomes. Such vehicles are known in the art.

The transfection of IMP cells may be performed in vitro or ex vivo. Alternatively, stable transfection may be perfomed at the MC stage allowing IMP cells expressing the transgene to be differentiated from them. The IMP cells are transfected with a nucleic acid encoding the agent. For instance, viral particles or other vectors encoding the agent may be employed. Methods for doing this are known in the art.

The nucleic acid gives rise to expression of the agent in the IMP cells. The nucleic acid molecule will preferably comprise a promoter which is operably linked to the sequences encoding the agent and which is active in the IMP cells or which can be induced in the IMP cells.

In a particularly preferred embodiment, the nucleic acid encoding the agent may be delivered via a viral particle. The viral particle may comprise a targeting molecule to ensure efficient transfection. The targeting molecule will typically be provided wholly or partly on the surface of the virus in order for the molecule to be able to target the virus to the IMP cells.

Any suitable virus may be used in such embodiments. The virus may, for example, be a retrovirus, a lentivirus, an adenovirus, an adeno-associated virus, a vaccinia virus or a herpes simplex virus. In a particularly preferred embodiment the virus may be a lentivirus. The lentivirus may be a modified HIV virus suitable for use in delivering genes. The lentivirus may be a SIV, FIV, or equine infectious anemia virus (EQIA) based vector. The virus may be a moloney murine leukaemia virus (MMLV). The viruses used in the invention are preferably replication deficient.

Viral particles do not have to be used. Any vector capable of transfecting the IMP cells of the invention may be used, such as conventional plasmid DNA or RNA transfection.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectAmine, fugene and transfectam.

The cell may be loaded or tranfected under suitable conditions. The cell and agent or vector may, for example, be contacted for between five minutes and ten days, preferably from an hour to five days, more preferably from five hours to two days and even more preferably from twelve hours to one day.

The invention also provides IMP cells which have been loaded or transfected with an agent as discussed above. Such IMP cells may be used in the therapeutic embodiments of the invention.

In some embodiments, MCs may be recovered from a patient, converted into IMP cells using the invention, loaded or transfected in vitro and then returned to the same patient. In such instances, the IMP cells employed in the invention, will be autologous cells and fully matched with the patient. In a preferred case, the cells employed in the invention are recovered from a patient and utilised ex vivo and subsequently returned to the same patient.

Pharmaceutical Compositions and Administration

The invention additionally provides a pharmaceutical composition comprising an IMP cell of the invention or a population of the invention in combination with a pharmaceutically acceptable carrier or diluent, (ii) one or more lipsomes and/or (iii) one or more microbubbles. The composition may comprise (i); (ii); (iii); (i) and (ii); (i) and (iii); (ii) and (iii); or (i), (ii) and (iii). The IMP cell or population are preferably contained with the one or more liposomes and/or one or more microbubbles. Any number of liposomes and/or microbubbles may be present. Any of the numbers discussed above with reference to the population of the invention are equally application to the lipsomes and/or microbubbles. A lipsome or microbubble may contain one IMP cell or more than one IMP cell.

The composition may comprise any of the IMP cells or populations mentioned herein and, in some embodiments, the nucleic acid molecules, vectors, or viruses described herein. The invention provides a method of repairing a damaged tissue in a patient comprising administering to the patient an effective amount of a pharmaceutical composition of the invention. Any of the therapeutic embodiments discussed above equally apply to this embodiment.

The various compositions of the invention may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19$^{th}$ Edition, Mack Publishing Company, Eastern Pennsylvania, USA.

The cells may be administered by any route. Suitable routes include, but are not limited to, intravenous, intramuscular, intraperitoneal or other appropriate administration routes. If the damaged tissue is cardiac tissue, the cells may be administered via an endomyocardial, epimyocardial, intraventicular, intracoronary, retrograde coronary sinus, intra-arterial, intra-pericardial or intravenous route. If the damaged tissue is bone, the cells may be administered via an intraosseous route or to the site of the injury, such as a fracture, or disease. If the damaged tissue is cartilage, tendon, ligament, liver, kidney or lung tissue, the cells may be administered directly into the tissue. If the damaged tissue is lung tissue, the cells may be introduced via an intra-pulmonary route. If the damaged tissue is liver or kidney, the cells may be introduced via an intra-peritoneal route. The cells are preferably administered intravenously.

Compositions may be prepared together with a physiologically acceptable carrier or diluent. Typically, such compositions are prepared as liquid suspensions of cells. The cells may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions of the invention may contain minor amounts of auxiliary substances such as wetting or emulsifying agents, pH buffering agents, and/or adjuvants which enhance effectiveness. The composition preferably comprises human serum albumin.

One suitable carrier or diluents is Plasma-Lyte A®. This is a sterile, nonpyrogenic isotonic solution for intravenous administration. Each 100 mL contains 526 mg of Sodium Chloride, USP (NaCl); 502 mg of Sodium Gluconate (C6H11NaO7); 368 mg of Sodium Acetate Trihydrate, USP (C2H3NaO2.3H2O); 37 mg of Potassium Chloride, USP (KCl); and 30 mg of Magnesium Chloride, USP (MgCl2.6H2O). It contains no antimicrobial agents. The pH is adjusted with sodium hydroxide. The pH is 7.4 (6.5 to 8.0).

The IMP cells may be contained within one or more liposomes and/or one or more microbubbles. Suitable liposomes are known in the art. Suitable liposomes are disclosed in, for example, Akbarzadeh et al. Nanoscale Research Letters 2013, 8:102 and Meghana et al. International Journal Of Pharmaceutical And Chemical Sciences, 2012, 1(1): 1-10. Suitable lipids for use in forming liposomes are discussed below with reference to microbubbles.

Microbubbles, their formation and biomedical uses are known in the art (e.g. Sirsi and Borden, Bubble Sci Eng Technol. November 2009; 1(1-2): 3-17). Microbubbles are bubbles smaller than one millimetre in diameter and larger than one micrometre in diameter. The microbubble used in the present invention is preferably 8 µm or less in diameter, such as 7 µm or less in diameter, 6 µm or less in diameter, 5 µm or less in diameter, 4 µm or less in diameter, 3 µm or less in diameter or 2 µm or less in diameter.

The microbubble may be formed from any substance. The general composition of a microbubble is a gas core stabilised by a shell. The gas core may comprise air or a heavy gas, such as perfluorocarbon, nitrogen or perflouropropane. Heavy gases are less water soluble and so are less likely to leak out from the microbubble leading to microbubble dissolution. Microbubbles with heavy gas cores typically last longer in circulation.

The shell may be formed from any material. The shell material preferably comprises a protein, a surfactant, a lipid, a polymer or a mixture thereof.

Suitable proteins, include but are not limited to, albumin, lysozyme and avidin. Proteins within the shell may be chemically-crosslinked, for instance by cysteine-cysteine linkage. Other crosslinkages are known in the art.

Suitable surfactants include, but are not limited to, sorbitan monopalmitate (such as SPAN-40), polysorbate detergents (such as TWEEN-40), mixtures of SPAN-40 and TWEEN-40 and sucrose stearate (mono- and di-ester).

Suitable polymers include, but are not limited to, alginate polymers, double ester polymers of ethylidene, the copolymer poly(D,L-lactide-co-glycolide) (PLGA), poly(vinyl alcohol) (PVA), the copolymer polyperfluorooctyloxycaronyl-poly(lactic acid) (PLA-PFO) and other block copolymers. Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid headgroups.

Any lipid material that forms a microbubble may be used. The lipid composition is chosen such that the microbubble has the required properties, such surface charge, packing density or mechanical properties. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipid typically comprises a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the ligands, receptors ro antibodies as discussed above.

The lipid composition may comprise one or more additives that will affect the properties of the microbubble. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

The microbubble shell is preferably formed from a phospholipid. Suitable phospholipids are known in the art.

There are several commercially available lipid shell microbubble formulations such as Definity (Lantheus Medical Imaging) and Sonovue® (Bracco Diagnostics).

The microbubble may also be formed from a polymer-surfactant hybrid that involves forming polyelectrolyte multilayer (PEM) shells on a preformed microbubble. The preformed microbubble is coated with a charged surfactant or protein layer, which serves as a substrate for PEM deposition. The layer-by-layer assembly technique is used to sequentially adsorb oppositely charged polyions to the microbubble shell. For instance, PEM can be deposited onto microbubbles using poly(allylamine hydrochloride) (PAH) and poly(styrene sulfonate) (PSS) for the polyion pair. PEM microbubbles with phospholipid containing the cationic headgroup trimethylammonium propane (TAP) as the underlying shell and DNA and poly(L-lysine) (PLL) as the polyion pair have also been developed.

The microbubble is typically formed by providing an interface between a gas and a microbubble shell material. Any of the materials discussed above may be used. Some materials, such as phospholipids, spontaneously form microbubbles. Phospholipids self assemble into a microbubble. Other materials require sonication of the interface, i.e. the application of sound energy or sonic waves to the interface. Ultrasonic waves are typically used. Suitable methods are known in the art for sonication.

The microbubble may be loaded with the IMP cells after formation of the microbubble or during formation of the microbubble.

The IMP cells are administered in a manner compatible with the dosage formulation and in such amount will be therapeutically effective. The quantity to be administered depends on the subject to be treated, capacity of the subject's immune system and the degree repair desired. Precise amounts of IMP cells required to be administered may depend on the judgement of the practitioner and may be peculiar to each subject.

Any suitable number of cells may be administered to a subject. For example, at least, or about, $0.2 \times 10^6$, $0.25 \times 10^6$, $0.5 \times 10^6$, $1.5 \times 10^6$, $4.0 \times 10^6$ or $5.0 \times 10^6$ cells per kg of patient may administered. For example, at least, or about, $10^5$, $10^6$, $10^7$, $10^8$, $10^9$ cells may be administered. As a guide, the number of cells of the invention to be administered may be from $10^5$ to $10^9$, preferably from $10^6$ to $10^8$. Typically, up to $2 \times 10^8$ IMP cells are administered to each patient. Any of the specific numbers discussed above with reference to the populations of the invention may be administered. In such cases where cells are administered or present, culture medium may be present to facilitate the survival of the cells. In some cases the cells of the invention may be provided in frozen aliquots and substances such as DMSO may be present to facilitate survival during freezing. Such frozen cells will typically be thawed and then placed in a buffer or medium either for maintenance or for administration.

Hybrid Composition

One or more IMP cells of the invention may form part of a hybrid composition as disclosed in the UK Application being filed concurrently with this application (CTL Ref: FIBRE1) and are preferably administered to a patient as part of such a composition. In particular, the invention provides a hybrid composition, which comprises:

(a) one or more biocompatible fibres;
(b) one or more IMP cells of the invention; and
(c) one or more biocompatible components which (i) attach the one or more therapeutic cells to the one or more fibres and/or embed the one or more therapeutic cells and the one or more fibres and/or (ii) are capable of attaching the composition to a tissue.

The hybrid composition of the invention comprises one or more biocompatible fibres. A fibre is biocompatible if it does not cause any adverse reactions or side effects when contacted with a damaged tissue.

Any number of biocompatible fibres may be present in the composition. The composition may comprise only one fibre. The composition typically comprises more than one fibre, such at least 2, at least 5, at least 10, at least 20, at least 30, at least 40, at least 50, at least 100, at least 200, at least 500 fibres, at least 1000 fibres or even more fibres.

Suitable biocompatible fibres are known in the art. The one or more biocompatible fibres may be natural or synthetic. Preferred biocompatible fibres include, but are not limited to, cellulose fibres, collagen fibres, collagen-glycosaminoglycan fibres, gelatin fibres, silk fibroin fibres, one or more fibrin fibres, chitosan fibres, starch fibres, alginate fibres, hyaluronan fibres, poloaxmer fibres or a combination thereof. The glycosaminoglycan is preferably chondroitin. The cellulose is preferably carboxymethylcellulose, hydroxypropylmethylcellulose or methylcellulose. The poloaxmer is preferably pluronic acid, optionally Pluronic F-127.

If more than one fibre is present in the composition, the population of fibres may be homogenous. In other words, all of the fibres in the population may be the same type of fibre, e.g. cellulose fibres. Alternatively, the population of fibres may be heterogeneous. In other words, the population of fibres may contain different types of fibre, such cellulose fibres and collagen fibres.

The one or more fibres may be any length. The one or more fibres are preferably approximately the same length as the depth of the damage in the tissue which is to be treated using the composition. The length of one or more fibres is preferably designed such that the composition can penetrate a damaged tissue to a prescribed depth. The one or more fibres may be any length. The lower limit of the length of the one or more fibres is typically determined by the diameter of the one or more therapeutic cells. Suitable lengths include, but are not limited to, at least 1 μm in length, at least 10 μm in length, at least 100 μm in length, at least 500 μm in length, at least 1 mm in length, at least 10 mm (1 cm) in length, at least 100 mm (10 cm) in length, at least 500 mm (50 cm) in length or at least 1000 mm (100 cm or 1 m) in length. The one or more fibres may be even longer. For instance, the one or more fibres may be up to 5 m or 10 m in length, for instance if being used to repair damage along the human intestinal tract, or even longer if being used in larger animals, such as horses. The length of the one or more fibres is typically determined by their intended use and/or their ability to be manipulated, for instance by a surgeon, by a robot or via some other means, such as magnetically.

The one or more fibres may be charged. The one or more fibres are preferably positively-charged. The one or more fibres are preferably negatively-charged.

The one or more fibres may be magnetic. The one or more fibres may be modified to include one or more magnetic atoms or groups. This allows magnetic targeting of the composition. The magnetic atoms or groups may be paramagnetic or superparamagnetic. Suitable atoms or groups include, but are not limited to, gold atoms, iron atoms, cobalt atoms, nickel atoms and a metal chelating groups, such as nitrilotriacetic acid, containing any of these atoms. The metal chelating group may, for instance, comprise a group selected from —C(=O)O—, —C—O—C—, —C(=O), —NH—, —C(=O)—NH, —C(=O)—CH$_2$—I, —S(=O)$_2$— and —S—.

The composition also comprises one or more biocompatible components. The one or more biocompatible components (i) attach the one or more therapeutic cells to the one or more fibres and/or embed the one or more therapeutic cells and the one or more fibres and/or (ii) are capable of attaching the composition to a tissue. The one or more biocompatible components may (a) attach the one or more therapeutic cells to the one or more fibres, (b) embed the one or more therapeutic cells and the one or more fibres, (c) be capable of attaching the composition to a tissue, (d) attach the one or more therapeutic cells to the one or more fibres and embed the one or more therapeutic cells and the one or more fibres, (e) attach the one or more therapeutic cells to the one or more fibres and be capable of attaching the composition to a tissue, (f) embed the one or more therapeutic cells and the one or more fibres and be capable of attaching the composition to a tissue or (g) attach the one or more therapeutic cells to the one or more fibres, embed the one or more therapeutic cells and the one or more fibres and be capable of attaching the composition to a tissue.

A component is biocompatible if it does not cause any adverse reactions or side effects when contacted with a damaged tissue.

Any number of biocompatible components may be present in the composition. The composition typically comprises only one component or two components. The composition may comprise more than two components, such as at least 3, at least 5, at least 10, at least 20, at least 30, at least 40, at least 50 components or even more components.

The one or more biocompatible components preferably comprise a biocompatible adhesive which attaches the one or more therapeutic cells to the one or more fibres. The biocompatible adhesive may attach the one or more therapeutic cells (a) on the surface of the one or more fibres, (b) within the one or more fibres or (c) both on the surface of and within the one or more fibres.

The biocompatible adhesive may be natural or synthetic. Suitable biocompatible adhesives are known in the art. Suitable adhesives include, but are not limited to, fibrin, fibrin gel, integrin, integrin gel, cadherin and cadherin gel.

The one or more biocompatible components preferably comprise a biocompatible gel which embeds the one or more therapeutic cells and the one or more fibres. Suitable biocompatible gels are known in the art. The biocompatible gel may be natural or synthetic. Preferred biocompatible gels include, but are not limited to, a cellulose gel, a collagen gel, a gelatin gel, a fibrin gel, a chitosan gel, a starch gel, an alginate gel, a hyaluronan gel, an agarose gel, a poloaxmer gel or a combination thereof.

The cellulose gel may be formed from any of the celluloses discussed above. The cellulose polymer concentration is preferably from about 1.5% (w/w) to about 4.0% (w/w), such as from about 2.0% (w/w) to about 3.0% (w/w). The cellulose polymer preferably has a molecular weight of from about 450,000 to about 4,000,000, such as from about 500,000 to about 3,500,000, from about 500,000 to about 3,000,000 or from about 750,000 to about 2,500,000 or from about 1000,000 to about 2,000,000.

The poloaxmer gel is preferably a pluronic acid gel, optionally a Pluronic F-127 gel.

The adhesive and/or gel preferably has a viscosity in the range of 1000 to 500,000 mPa·s (cps) at room temperature, such as from about 1500 to about 450,000 mPa·s at room temperature, from about 2000 to about 400,000 mPa·s at room temperature, from about 2500 to about 350,000 mPa·s at room temperature, from about 5000 to about 300,000 mPa·s at room temperature, from about 10,000 to about 250,000 mPa·s at room temperature, from about 50,000 to about 200,000 mPa·s at room temperature or from about 50,000 to about 150,000 mPa·s at room temperature.

Viscosity is a measure of the resistance of the adhesive and/or gel to being deformed by either shear stress or tensile stress. Viscosity can be measured using any method known in the art. Suitable methods include, but are not limited to, using a viscometer or a rheometer.

Room temperature is typically from about 18° C. to about 25° C., such as from about 19° C. to about 24° C. or from about 20° C. to about 23° C. or from about 21° C. to about 22° C. Room temperature is preferably any of 18° C., 19° C., 20° C., 21° C., 22° C., 23° C., 24° C. and 25° C. Viscosity is most preferably measured at 25° C.

The one or more biocompatible components preferably comprises a biocompatible adhesive which attaches the one or more therapeutic cells to the one or more fibres and a biocompatible gel which embeds the one or more therapeutic cells and the one or more fibres. For instance, the composition may comprise a fibrin gel which attaches the one or more therapeutic cells to the one or more fibres and a cellulose gel which embeds the one or more therapeutic cells and the one or more fibres.

In any of the embodiments discussed above, the biocompatible adhesive and/or the biocompatible gel preferably comprises platelet lysate. For instance, the adhesive and/or the gel may be a platelet lystae gel. Platelet lysate refers to the combination of natural growth factors contained in platelets that has been released through lysing those platelets. Lysis can be accomplished through chemical means (i.e. $CaCl_2$), osmotic means (use of distilled $H_2O$) or through freezing/thawing procedures. Platelet lysate can be derived from whole blood as described in U.S. Pat. No. 5,198,357. Platelet lysate is preferably prepared as described in PCT/GB12/052911 (published as WO 2013/076507). For instance, it may be prepared by subjecting a population of platelets to at least one freeze-thaw cycle, wherein the freeze portion of each cycle is carried out at a temperature lower than or equal to −78° C.

The adhesive and/or gel preferably comprises (a) platelet lysate, (b) at least one pharmaceutically acceptable polymer and (c) at least one pharmaceutically acceptable positively charged chemical species selected from the group consisting of lysine, arginine, histidine, aspartic acid, glutamic acid, alanine, methionine, proline, serine, asparagine, cysteine, polyamino acids, protamine, aminoguanidine, zinc ions and magnesium ions, wherein the composition is an aqueous gel having a viscosity in the range of 1000 to 500,000 mPa·s (cps) at room temperature. The pharmaceutically acceptable polymer is preferably cellulose or a poloaxmer. It may be any of the celluloses and poloaxmers discussed above.

The platelet lysate is preferably human platelet lysate. Platelet lysate is discussed in more detail above.

The hybrid composition may be contained within one or more liposomes or one or more microbubbles. Such structures are known in the art.

The following Examples illustrate the invention.

EXAMPLES

Example 1

Bone Marrow and Peripheral Blood Isolation & Expansion of IMP Cells

A bone marrow sample was diluted with Hank Buffered Saline Solution and layered over Ficoll-Paque for the isolation of mononuclear cells (MCs) by centrifugation. The MCs were then re-suspended in Hank Buffered Saline Solution and counted using 0.4% trypan blue exclusion assay to assess cellular viability. Cells were seeded in T25 flasks (in 5 ml of cell culture media, αMEM, GlutaMAX, penicillin-streptomycin, platelet lysate, heparin), and incubated at 37° C., 5% CO2. On day 8 the media was changed. Cells were monitored daily for observation of IMP-like cells and, if present, harvested using cell dissociating solution according to manufacturer's instructions and sub-cultured in the same media as above. Cells were cryopreserved in passage 2 in culture media supplemented with 10% dimethyl sulfoxide to −80° C. and stored in liquid nitrogen for later use.

Example 2

HT-FACS Analysis

High-throughput fluorescence activated cell sorting (HT-FACS) analysis is a high-throughput screening platform which can rapidly characterize the cell surface phenotype of cells in suspension, with over 370 cell surface markers currently in the panel. This platform has undergone extensive validation and has been performed on many types of human tissues and cells. The panel consists of 375 human cell surface-specific antibodies arrayed in 96-well plates.

The aim was to determine the surface antigen expression profile of human IMPs of the invention and human MSCs obtained from Lonza®. The high-throughput-FACS (HT-FACS) platform allows the screening of 375 surface antigens.

One vial of cryopreserved PB-MSCs (1×106 cells/ml) was seeded in a T75 cm2 flask containing 15 mL of CTL media (37° C., 5% CO2). Cells were grown until confluence of 80-90% changing the media every 2-3 days. To passage the cells, the media was removed and cells were washed twice with PBS. Cells were treated with 3 ml of Trypsin 0.25% until detached. Eight ml of media were added to inactivate the trypsin and cells were collected by centrifugation at 400g for 5 min. Cells were re-suspended in 5 ml of media and seeded in a T175 cm2 flask containing 30 mL of CTL media (37° C., 5% CO2). Between 8 to 10 T175 cm2 flasks at 80-90% confluence were required to harvest 20-30 million cells (at passage 4) for the HT-FACS screening. In order to obtain a sufficient number of flow cytometry "events" per antibody, approximately 20 million viable cells is optimal. To collect the cells, the media was removed and cells were washed twice with PBS. Cells were treated with 5 ml of Trypsin 0.25% until detached. Media was added (8 ml) to inactivate the trypsin and collect the cells. Cells were centrifuged at 400 g for 5 min. The cell pellets were re-suspended (single-cell suspension) in 5 ml total of HBSS (Hank's Balanced Salt Solution minus calcium/magnesium, supplemented with 2 mM EDTA and 1% BSA). One aliquot of the sample (10 µl) was used to determine the total number of viable cells by using exclusion dye (0.2% trypan blue).

100 µl of sample were loaded into each well (about 40,000 cells per well assuring the collection of 10,000 to 20,000 events in the FACS). The samples were run in a BD FACSDiva upgraded with a BD High Throughput Sampler (automated sampler). The analysis of flow cytometry data were performed using FlowJo Software. The results were provided in plots, and an Excel spreadsheet containing the percentage of positive cells and median fluorescence intensity (MFI) for each antibody.

TABLE 1

Results of the HT-FACS analysis

| # | Marker | Alternative name: | % IMP | % Lonza® MSC |
|---|---|---|---|---|
| 1 | BLTR-1 | | 6.7 | 1.37 |
| 2 | B2-microglobulin | | 99.8 | 100 |
| 3 | CA9 | Carbonic anhydrase 9 | 5.22 | 0 |
| 4 | CDH3 | Cadherin-3/P-Cadherin | 2.93 | 0.475 |
| 5 | CDH6 | Cadherin-6 | 0.6 | 0.235 |
| 6 | CDH11 | Cadherin-11 | 61.6 | 0.88 |
| 7 | CDw93 | | 11.5 | 4.75 |
| 8 | CDw198 | CCR8 | 10.6 | 5.17 |
| 9 | CDw199 | CCR9 | 17.2 | 2.54 |
| 10 | CDw210 | Interleukin 10 receptor, alpha subunit (IL10RA) | 10.8 | 0.622 |
| 11 | CDw218a | interleukin-18 receptor 1 (IL18R1) | 0.384 | 0 |
| 12 | CDw329 | Sialic acid-binding Ig-like lectin 9 (Siglec 9) | 0.182 | 0 |
| 13 | CD1a | | 0.338 | 0.28 |
| 14 | CD1b | | 0.766 | 0.745 |
| 15 | CD1c | | 15.7 | 0.926 |
| 16 | CD1d | R3G1 | 2.7 | 0 |
| 17 | CD2 | LFA-2 | 0.292 | 0.526 |
| 18 | CD3 | | 0.158 | 0 |
| 19 | CD3e | | 0.087 | 0 |
| 20 | CD4 | | 1.11 | 0.157 |
| 21 | CD5 | Leu-1 | 0.151 | 0.34 |
| 22 | CD6 | | 1.04 | 2.68 |
| 23 | CD7 | GP40/Leu-9 | 0.239 | 0.24 |
| 24 | CD8 | | 0.214 | 0 |
| 25 | CD8b | | 4.34 | 0.705 |
| 26 | CD9 | BTCC-1 | 38.1 | 51.9 |
| 27 | CD10 | Neprilysin (NEP)/common acute lymphoblastic leukemia antigen (CALLA) | 90.6 | 87.1 |
| 28 | CD11a | ITGAL, LFA-1 | 1.57 | 0 |
| 29 | CD11b | Integrin alpha M (ITGAM) | 6.24 | 0 |

TABLE 1-continued

Results of the HT-FACS analysis

| # | Marker | Alternative name: | % IMP | % Lonza® MSC |
|---|---|---|---|---|
| 30 | CD11c | Integrin, alpha X (ITGAX) | 1.8 | 0 |
| 31 | CD13 | Alanine aminopeptidase (ANPEP) | 100 | 100 |
| 32 | CD14 |  | 8.03 | 6.25 |
| 33 | CD15 | SSEA-1 | 0.137 | 0.474 |
| 34 | CD16 | Fc Receptor | 10.1 | 3.73 |
| 35 | CD16b | Fc fragment of IgG, low affinity Mb, receptor (FCGR3B) | 0.331 | 0 |
| 36 | CD17 | Lactosylceramide (LacCer) | 20.9 | 0.462 |
| 37 | CD18 | Integrin beta-2 | 0.65 | 0 |
| 38 | CD19 |  | 0.21 | 0 |
| 39 | CD20 |  | 0.176 | 0 |
| 40 | CD21 | Complement receptor type 2 (Cr2)/ Epstein-Barr virus receptor (EBV R) | 0.66 | 0 |
| 41 | CD22 | BL-CAM/Siglec-2 | 0.596 | 0 |
| 42 | CD23 | Low affinity immunoglobulin epsilon Fc receptor (FCER2) | 0.551 | 0.234 |
| 43 | CD24 |  | 0.987 | 4 |
| 44 | CD25 | Interleukin-2 receptor subunit alpha (IL2RA) | 1.44 | 1.67 |
| 45 | CD26 | Dipeptidyl peptidase IV (DPP4) | 21.3 | 6.33 |
| 46 | CD27 | Tumor necrosis factor receptor superfamily member 7 (TNFRSF7) | 0.409 | 0 |
| 47 | CD28 |  | 0.643 | 0 |
| 48 | CD29 | Integrin beta-1 (ITGB1) | 100 | 100 |
| 49 | CD30 | Tumor necrosis factor receptor superfamily member 8 (TNFRSF8) | 0.446 | 0 |
| 50 | CD31 | PECAM | 1.29 | 0.214 |
| 51 | CD32 | Low affinity immunoglobulin gamma Fc region receptor II-b | 0.698 | 3.46 |
| 52 | CD33 | Siglec-3 | 1.25 | 0.372 |
| 53 | CD34 |  | 0.287 | 0.885 |
| 54 | CD35 | Complement receptor type 1 (Cr1) | 0.134 | 0 |
| 55 | CD36 | Platelet glycoprotein 4/Thrombospondin receptor | 0.458 | 3.57 |
| 56 | CD37 | Tetraspanin-26 (TSPAN26) | 0.0917 | 0.182 |
| 57 | CD38 | ADP-ribosyl cyclase 1 | 0.28 | 0 |
| 58 | CD39 | Ectonucleoside triphosphate diphosphohydrolase NTPdase 1 | 0.126 | 21.8 |
| 59 | CD40 | Tumor necrosis factor receptor superfamily member 5 (TNFRSF5) | 0.132 | 3.12 |
| 60 | CD41a |  | 0.293 | 0 |
| 61 | CD41b |  | 0.075 | 0 |
| 62 | CD42a | Platelet glycoprotein IX | 0.528 | 0.131 |
| 63 | CD42b | Platelet glycoprotein Ib alpha chain | 7.29 | 0 |
| 64 | CD43 | Leukosialin | 0.406 | 1.81 |
| 65 | CD44 | Epican | 99.9 | 99.7 |
| 66 | CD45 | Receptor-type tyrosine-protein phosphatase C, Leukocyte common antigen | 0.271 | 0 |
| 67 | CD45RA |  | 5.18 | 2.99 |
| 68 | CD45RB |  | 0.283 | 0.671 |
| 69 | CD45RO |  | 0.57 | 0 |
| 70 | CD46 | Membrane cofactor protein, Trophoblast leukocyte common antigen | 78.1 | 22.5 |
| 71 | CD47 | Antigenic surface determinant protein OA3 | 92.3 | 99.9 |
| 72 | CD48 | SLAM F2 | 0.141 | 0.125 |
| 73 | CD49a | Integrin alpha-1 (ITGA1) | 24 | 51.5 |
| 74 | CD49b | Integrin alpha-2 (ITGA2) | 97.7 | 45.8 |
| 75 | CD49c | Integrin alpha-3 (ITGA3) | 99.9 | 99.6 |
| 76 | CD49d | Integrin alpha-4 (ITGA4) | 93.7 | 26 |
| 77 | CD49e | Integrin alpha-5 (ITGA5) | 100 | 99.8 |
| 78 | CD49f | Integrin alpha-6 (ITGA6) | 93.3 | 24.1 |
| 79 | CD50 | ICAM-3 | 0.244 | 0.8 |
| 80 | CD51/CD61 |  | 92.7 | 68 |
| 81 | CD52 | CAMPATH-1 antigen | 0.218 | 0.128 |
| 82 | CD53 |  | 1.66 | 0.292 |
| 83 | CD54 | ICAM-1 | 23.1 | 23.7 |
| 84 | CD55 | Complement decay-accelerating factor | 94.5 | 52.5 |
| 85 | CD56 | NCAM | 3.05 | 4.71 |
| 86 | CD57 | Killer cell lectin-like receptor subfamily G member 1 | 0.193 | 0 |
| 87 | CD58 | LFA-3 | 99.7 | 98.1 |
| 88 | CD59 | Protectin | 100 | 100 |
| 89 | CD60b |  | 34 | 10.9 |
| 90 | CD61 | Integrin beta-3 ITGB3 | 81.8 | 56.7 |
| 91 | CD62E | E-Selectin Ligand | 2.33 | 1.03 |
| 92 | CD62L | L-Selectin Ligand | 0.432 | 0.151 |

TABLE 1-continued

Results of the HT-FACS analysis

| # Marker | Alternative name: | % IMP | % Lonza® MSC |
|---|---|---|---|
| 93 CD62P | P-Selectin Ligand | 0.325 | 0.924 |
| 94 CD63 | Lysosomal-associated membrane protein 3 (LAMP-3) | 99.1 | 95.8 |
| 95 CD64 | High affinity immunoglobulin gamma Fc receptor I (Fc-gamma RI) | 0.263 | 0.225 |
| 96 CD65 | | 0.825 | 0 |
| 97 CD65s | | 7.62 | 0.539 |
| 98 CD66 | Pregnancy-specific beta-1-glycoprotein 1 PSGB1 | 0.474 | 0.737 |
| 99 CD66b | | 0.129 | 0 |
| 100 CD66c | Carcinoembryonic antigen-related cell adhesion molecule 6 | 23.4 | 7.33 |
| 101 CD66d | Carcinoembryonic antigen-related cell adhesion molecule 3 | 2.06 | 0.322 |
| 102 CD66e | Carcinoembryonic antigen-related cell adhesion molecule 5 | 56.1 | 13.6 |
| 103 CD69 | Activation inducer molecule (AIM) | 0.296 | 0.279 |
| 104 CD70 | Tumor necrosis factor ligand superfamily member 7 (TNFSF7) | 0.36 | 0.187 |
| 105 CD71 | Transferrin receptor protein 1 | 51 | 4.71 |
| 106 CD72 | | 0.036 | 0.334 |
| 107 CD73 | 5'-nucleotidase/SH3/SH4 | 100 | 99.8 |
| 108 CD74 | HLA class II histocompatibility antigen gamma chain | 0.177 | 0.587 |
| 109 CD75 | Beta-galactoside alpha-2,6-sialyltransferase 1 | 0.0789 | 0.304 |
| 110 CD77 | Lactosylceramide 4-alpha-galactosyltransferase | 7.15 | 2.4 |
| 111 CD79a | B-cell antigen receptor complex-associated protein alpha chain | 15.4 | 0.45 |
| 112 CD79b | B-cell antigen receptor complex-associated protein beta chain | 4.87 | 0.317 |
| 113 CD80 | Activation B7-1 antigen | 2.94 | 4.57 |
| 114 CD81 | Tetraspanin-28 | 100 | 99.9 |
| 115 CD82 | Tetraspanin-27 | 96.3 | 82.7 |
| 116 CD83 | | 27.9 | 1.34 |
| 117 CD84 | SLAM F5 | 7.94 | 4.1 |
| 118 CD85a | Leukocyte immunoglobulin-like receptor subfamily B member 3 (LIR-3) | 6.76 | 0.971 |
| 119 CD85d | Leukocyte immunoglobulin-like receptor subfamily B member 3 (LIR-2) | 17 | 0.98 |
| 120 CD85g | Leukocyte immunoglobulin-like receptor subfamily A member 4 | 47.2 | 6.15 |
| 121 CD85h | Leukocyte immunoglobulin-like receptor subfamily A member 2 (LILRA2) | 15.6 | 0 |
| 122 CD85j | Leukocyte immunoglobulin-like receptor subfamily B member 1 (LIR-1) | 20.6 | 0.221 |
| 123 CD86 | | 24.7 | 0.702 |
| 124 CD87 | Urokinase plasminogen activator surface receptor (uPAR) | 0.178 | 1.61 |
| 125 CD88 | C5a anaphylatoxin chemotactic receptor 1 | 1.32 | 0.352 |
| 126 CD89 | Immunoglobulin alpha Fc receptor | 5.73 | 0.244 |
| 127 CD90 | Thy-1 membrane glycoprotein | 100 | 99.3 |
| 128 CD91 | Prolow-density lipoprotein receptor-related protein 1 (LRP-1) | 95.5 | 63.4 |
| 129 CD92 | Choline transporter-like protein 1 | 35.4 | 33.3 |
| 130 CD94 | Natural killer cells antigen CD94 KLRD1 | 0.121 | 0.321 |
| 131 CD95 | CD95L (Ligand)/Tumor necrosis factor ligand superfamily member 6 (TNFSF6) | 98.9 | 66.7 |
| 132 CD96 | T-cell surface protein tactile | 21 | 2.63 |
| 133 CD97 | | 1.64 | 0.434 |
| 134 CD98 | Large neutral amino acids transporter small subunit 1 | 100 | 99.9 |
| 135 CD99 | T-cell surface glycoprotein E2 | 24.8 | 0.224 |
| 136 CD100 | Semaphorin-4D | 0.103 | 0.132 |
| 137 CD101 | Immunoglobulin superfamily member 2 (IgSF2) | 0.29 | 0 |
| 138 CD102 | ICAM-2 | 9.24 | 2.91 |
| 139 CD103 | Integrin alpha-E (ITGAE) | 0.152 | 0.297 |
| 140 CD104 | Integrin beta-4 (ITGB4) | 4.06 | 99.3 |
| 141 CD105 | Endoglin (SH2) | 99.9 | 100 |
| 142 CD106 | VCAM | 6.93 | 4.64 |
| 143 CD107a | Lysosome-associated membrane glycoprotein 1 (LAMP-1) | 0.717 | 0.337 |
| 144 CD107b | Lysosome-associated membrane glycoprotein 2 (LAMP-2) | 0.221 | 0.225 |
| 145 CD108 | Semaphorin-7A | 99.7 | 78 |
| 146 CD109 | | 1.89 | 0.253 |

TABLE 1-continued

Results of the HT-FACS analysis

| # | Marker | Alternative name: | % IMP | % Lonza® MSC |
|---|---|---|---|---|
| 147 | CD110 | Thrombopoietin receptor (TPO-R) | 55.6 | 16.6 |
| 148 | CD111 | Herpes virus entry mediator C | 90.7 | 0 |
| 149 | CD112 | Poliovirus receptor-related protein 2 | 12.1 | 0.64 |
| 150 | CD114 | Granulocyte colony-stimulating factor receptor (GCSFR/CSF3R) | 54.9 | 4.83 |
| 151 | CD115 | Macrophage colony-stimulating factor 1 receptor CSF-1 receptor (CSF-1-R) | 8.41 | 0 |
| 152 | CD116 | Granulocyte-macrophage colony-stimulating factor receptor subunit alpha GM-CSF-R-alpha | 17 | 2.61 |
| 153 | CD117 | Mast/stem cell growth factor receptor Kit (c-kit) | 31.5 | 2.56 |
| 154 | CD118 | Leukemia inhibitory factor receptor (LIF-R) | 67.4 | 0 |
| 155 | CD119 | Interferon gamma receptor 1 (IFNgammaR) | 78.5 | 24.8 |
| 156 | CD120a | Tumor necrosis factor receptor superfamily member 1A (TNFR1) | 38.1 | 0 |
| 157 | CD120b | Tumor necrosis factor receptor superfamily member 1B (TNFR2) | 1.11 | 0.297 |
| 158 | CD121b | Interleukin-1 receptor type 2 (IL1R2) | 39.8 | 2.75 |
| 159 | CD122 | Interleukin-2 receptor subunit beta (IL2RB) | 41.7 | 4.56 |
| 160 | CD123 | Interleukin-3 receptor subunit alpha (IL3RA) | 46.9 | 7.06 |
| 161 | CD124 | Interleukin-4 receptor subunit alpha IL4RA) | 1.52 | 0.225 |
| 162 | CD125 | Interleukin-5 receptor subunit alpha (IL5RA) | 19.5 | 0 |
| 163 | CD126 | Interleukin-6 receptor subunit alpha (IL-6R 1) | 7.05 | 0.709 |
| 164 | CD127 | Interleukin-7 receptor subunit alpha (IL7RA) | 18.5 | 12.5 |
| 165 | CD129 | Interleukin-9 receptor (IL9R) | 0.178 | 0 |
| 166 | CD130 | Interleukin-6 receptor subunit beta (IL6ST) | 83.6 | 8.15 |
| 167 | CD131 | Cytokine receptor common subunit beta | 0.684 | 0 |
| 168 | CD132 | Cytokine receptor common subunit gamma (IL2RG) | 78.8 | 3.43 |
| 169 | CD133 | AC-133 (Prominin-1) | 0.054 | 0 |
| 170 | CD134 | Tumor necrosis factor receptor superfamily member 4 (TNFSF4) | 8.15 | 1.29 |
| 171 | CD135 | Receptor-type tyrosine-protein kinase FLT3 | 5.18 | 0.575 |
| 172 | CD136 | Macrophage-stimulating protein receptor (MSP-R) | 0.302 | 0 |
| 173 | CD137 | Tumor necrosis factor receptor superfamily member 9 (TNFRSF9) | 0.392 | 0 |
| 174 | CD137L | Mouse? | 13.5 | 15.6 |
| 175 | CD138 | Syndecan-1 (SYND1) | 0.227 | 0 |
| 176 | CD140a | Platelet-derived growth factor receptor alpha (PDGFRA) | 4.1 | 0.98 |
| 177 | CD140b | Platelet-derived growth factor receptor beta (PDGFRB) | 89.1 | 97.8 |
| 178 | CD141 | Thrombomodulin | 21 | 0.385 |
| 179 | CD142 | Tissue factor/Thromboplastin | 0.478 | 0.555 |
| 180 | CD143 | Angiotensin-converting enzyme (ACE) | 29.3 | 0 |
| 181 | CD144 | Cadherin-5 | 0.0728 | 0.159 |
| 182 | CD146 | MUC18 | 94.2 | 89.5 |
| 183 | CD147 | Basigin | 100 | 100 |
| 184 | CD148 | Receptor-type tyrosine-protein phosphatase eta | 84.6 | 0 |
| 185 | CD150 | Signaling lymphocytic activation molecule (SLAMF-1) | 0.467 | 0.364 |
| 186 | CD151 | PETA-3 | 100 | 99.9 |
| 187 | CD152 | Cytotoxic T-lymphocyte protein 4 (CTLA-4) | 6.45 | 5.87 |
| 188 | CD153 | Tumor necrosis factor ligand superfamily member 8 (TNFSF8) | 10.9 | 1.19 |
| 189 | CD154 | CD40 Ligand | 0.357 | 0.893 |
| 190 | CD155 | Poliovirus receptor (PVR) | 99.8 | 100 |
| 191 | CD156b | Disintegrin and metalloproteinase domain-containing protein 17 (ADAM-17) | 81 | 36.4 |
| 192 | CD157 | ADP-ribosyl cyclase 2/Bone Marrow Stromal Antigen 1 (BST-1) | 0.713 | 6.33 |
| 193 | CD158a | Killer cell immunoglobulin-like receptor 2DL1 | 0.0919 | 0.22 |
| 194 | CD158b | Killer cell immunoglobulin-like receptor 2DL2 | 0.129 | 0.195 |
| 195 | CD158b2 | Killer cell immunoglobulin-like receptor 2DL3 | 2.54 | 0 |
| 196 | CD158d | Killer cell immunoglobulin-like receptor 2DL4 | 56.3 | 1.56 |
| 197 | CD158e2 | Killer cell immunoglobulin-like receptor 3DL1 | 0.254 | 0 |
| 198 | CD158f | Killer cell immunoglobulin-like receptor 2DL5A | 25 | 0 |
| 199 | CD158i | Killer cell immunoglobulin-like receptor 2DS4 | 21.9 | 3.12 |
| 200 | CD159a | NKG2-A/NKG2-B type II integral membrane protein (KLR-C1) | 6.57 | 0.462 |
| 201 | CD159c | NKG2-C type II integral membrane protein (KLR-C2) | 2.44 | 0.917 |
| 202 | CD160 | | 1.07 | 0.9 |
| 203 | CD161 | Killer cell lectin-like receptor subfamily B member 1 (KLRB1) | 5.95 | 3.64 |

TABLE 1-continued

Results of the HT-FACS analysis

| # Marker | Alternative name: | % IMP | % Lonza® MSC |
|---|---|---|---|
| 204 CD162 | P-selectin glycoprotein ligand 1 (PSGL-1) | 13.2 | 4.41 |
| 205 CD163 | Scavenger receptor cysteine-rich type 1 protein M130 | 0.197 | 0 |
| 206 CD164 | Sialomucin core protein 24 (MUC-24) | 11.9 | 27 |
| 207 CD165 | | 0.716 | 3.55 |
| 208 CD166 | Activated leukocyte cell adhesion molecule | 99.9 | 99.8 |
| 209 CD167 | Discoidin domain-containing receptor 2 (DDR2) | 0.496 | 7.69 |
| 210 CD169 | Sialoadhesin/Siglec-1 | 1.76 | 0.178 |
| 211 CD170 | Sialic acid-binding Ig-like lectin 5 (Siglec-5) | 11.9 | 74.3 |
| 212 CD171 | Neural cell adhesion molecule L1 (NCAM-L1) | 1.9 | 0 |
| 213 CD172a | Tyrosine-protein phosphatase non-receptor type substrate 1 (SHP-1) | 61.8 | 3.33 |
| 214 CD172b | Signal-regulatory protein beta-1 (SIRP-beta-1) | 0.0955 | 0.285 |
| 215 CD172g | Signal-regulatory protein gamma (SIRP-gamma) | 14.5 | 7.14 |
| 216 CD175s | | 96.2 | 27.1 |
| 217 CD177 | Human neutrophil alloantigen 2a (HNA-2a) | 0.477 | 0.46 |
| 218 CD178 | CD95L (Ligand)/Tumor necrosis factor ligand superfamily member 6 (TNFSF6) | 51.6 | 0.49 |
| 219 CD179a | | 6.31 | 1.84 |
| 220 CD180 | | 0.824 | 0.478 |
| 221 CD181 | CXCR1 | 85 | 2.55 |
| 222 CD182 | CXCR2 | 68.8 | 4.31 |
| 223 CD183 | CXCR3 | 3.08 | 0 |
| 224 CD184 | CXCR4 | 0.219 | 0.775 |
| 225 CD185 | CXCR5 | 6.04 | 1.39 |
| 226 CD186 | CXCR6 | 1.48 | 41.5 |
| 227 CD191 | CCR1 | 12.6 | 0 |
| 228 CD192 | CCR2 | 0.0662 | 0.0497 |
| 229 CD193 | CCR3 | 51 | 8.16 |
| 230 CD194 | CCR4 | 7.13 | 0 |
| 231 CD195 | CCR5 | 1.02 | 1.94 |
| 232 CD196 | CCR6 | 46.3 | 2.8 |
| 233 CD197 | CCR7 | 0.159 | 0 |
| 234 CD200 | OX-2 membrane glycoprotein (MOX-1)/(MOX-2) | 0.594 | 0.912 |
| 235 CD201 | Endothelial protein C receptor | 55.7 | 0.858 |
| 236 CD202b | Angiopoietin-1 receptor TIE2/TEK | 82.7 | 23.2 |
| 237 CD203c | Ectonucleotide pyrophosphatase/phosphodiesterase family member 3 (ENPP3) | 8.66 | 0 |
| 238 CD204 | Macrophage scavenger receptor types I and II (MSR1) | 13.7 | 1.44 |
| 239 CD205 | Lymphocyte antigen 75 (Ly-75) | 4.94 | 0 |
| 240 CD206 | Macrophage mannose receptor 1 (MMR) | 0.205 | 0 |
| 241 CD207 | C-type lectin domain family 4 member K (Langerin) | 0.0679 | 2.7 |
| 242 CD208 | Lysosome-associated membrane glycoprotein 3 (LAMP-3) | 3.27 | 0 |
| 243 CD209 | | 0.153 | 0 |
| 244 CD212 | Interleukin-12 receptor subunit beta-1 (IL12RB1) | 0.476 | 0.127 |
| 245 CD213a2 | Interleukin-13 receptor subunit alpha-2 (IL13RA2) | 8.7 | 8 |
| 246 CD215 | Interleukin-15 receptor subunit alpha | 14.6 | 0.86 |
| 247 CD217 | Interleukin-17 receptor A (IL17RA) | 29.8 | 35.8 |
| 248 CD218b | Interleukin-18 receptor accessory protein (IL-18 R-beta) | 23.4 | 0.463 |
| 249 CD220 | Insulin Receptor IR | 2.93 | 1.5 |
| 250 CD221 | Insulin-like growth factor 1 receptor IGF-1R | 3.16 | 1.1 |
| 251 CD222 | Insulin-like growth factor 2 receptor IGF-2R | 8.09 | 0.768 |
| 252 CD223 | Lymphocyte activation gene 3 protein (LAG-3) | 38.9 | 0 |
| 253 CD226 | DNAX accessory molecule 1 (DNAM-1) | 1.15 | 0.22 |
| 254 CD227 | Mucin-1 (MUC-1) | 4.87 | 5.79 |
| 255 CD229 | T-lymphocyte surface antigen Ly-9 | 0.579 | 5.56 |
| 256 CD230 | Major prion protein (PrP) | 99.9 | 100 |
| 257 CD231 | Tetraspanin-7 (TSPAN-7) | 34.2 | 34.8 |
| 258 CD234 | Duffy antigen/chemokine receptor (DARC) | 7.7 | 0.397 |
| 259 CD235a | Glycophorin-A | 55.8 | 5.11 |
| 260 CD243 (BC) | | 20.8 | 2.31 |
| 261 CD243 (BD) | | 0.208 | 0 |
| 262 CD244 | Natural killer cell receptor 2B4 | 0.548 | 0 |
| 263 CD245 | | 99.2 | 13.3 |
| 264 CD249 | Glutamyl aminopeptidase (EAP) | 19.7 | 0 |
| 265 CD252 | Tumor necrosis factor ligand superfamily member 4 (TNFSF4) | 21.4 | 20.6 |

TABLE 1-continued

Results of the HT-FACS analysis

| # Marker | Alternative name: | % IMP | % Lonza® MSC |
|---|---|---|---|
| 266 CD253 | Tumor necrosis factor ligand superfamily member10 (TNFSF10) | 44.1 | 7.07 |
| 267 CD254 | RANKL, TNFSF11 | 12.3 | 3.85 |
| 268 CD255 | | 10.1 | 0.437 |
| 269 CD256 | Tumor necrosis factor ligand superfamily member 13 (TNFSF13) | 7.94 | 0.792 |
| 270 CD257 | Tumor necrosis factor ligand superfamily member 13B (TNFSF13B) | 63.2 | 5.03 |
| 271 CD258 | Tumor necrosis factor ligand superfamily member 14 (TNFSF14) | 3.17 | 0 |
| 272 CD261 | Tumor necrosis factor receptor superfamily member 10A (TNFRSF10A) | 30.3 | 21.4 |
| 273 CD262 | Tumor necrosis factor receptor superfamily member 10B (TNFRSF10B) | 12.1 | 4.55 |
| 274 CD263 | Tumor necrosis factor receptor superfamily member 10C (TNFRSF10C) | 1.47 | 0 |
| 275 CD264 | Tumor necrosis factor receptor superfamily member 10D (TNFRSF10D) | 44.9 | 9.09 |
| 276 CD267 | Tumor necrosis factor receptor superfamily member 13B (TNFRSF13B) | 91.8 | 36.6 |
| 277 CD268 | Tumor necrosis factor receptor superfamily member 13C/(BAFF-R) | 64.6 | 13.5 |
| 278 CD269 | Tumor necrosis factor receptor superfamily member 17 (TNFRSF17) | 8.51 | 2.4 |
| 279 CD270 | Tumor necrosis factor receptor superfamily member 14 | 31.6 | 8.79 |
| 280 CD271 | Low-affinity nerve growth factor receptor (NGFR) | 1.63 | 10.4 |
| 281 CD272 | B- and T-lymphocyte attenuator | 33.2 | 12.3 |
| 282 CD273 | Programmed cell death 1 ligand 2 | 92.4 | 51.7 |
| 283 CD274 | Programmed cell death 1 ligand 1 | 23.9 | 1.12 |
| 284 CD275 | ICOS Ligand | 26 | 0.904 |
| 285 CD276 | 4Ig-B7-H3 | 100 | 97.8 |
| 286 CD277 | Butyrophilin subfamily 3 member A1 | 1.55 | 0 |
| 287 CD278 | Inducible T-cell costimulator | 0.147 | 0.0836 |
| 288 CD279 | Programmed cell death protein 1 | 5.5 | 0.492 |
| 289 CD281 | Toll-like receptor 1 | 54.7 | 2.12 |
| 290 CD282 | Toll-like receptor 2 | 0.101 | 0.529 |
| 291 CD283 | Toll-like receptor 3 | 68.9 | 6.92 |
| 292 CD284 | Toll-like receptor 4 | 7.94 | 0.84 |
| 293 CD286 | Toll-like receptor 6 | 76.9 | 11.4 |
| 294 CD288 | Toll-like receptor 8 | 85.6 | 11.2 |
| 295 CD289 | Toll-like receptor 9 | 11.3 | 0.359 |
| 296 CD290 | Toll-like receptor 11 | 45.1 | 9.5 |
| 297 CD292 | Bone morphogenetic protein receptor type-1A | 2.39 | 0.522 |
| 298 CD294 | Prostaglandin D2 receptor 2 | 8.81 | 34.1 |
| 299 CD295 | Leptin receptor (Lep-R) | 49 | 73.7 |
| 300 CD298 | Sodium/potassium-transporting ATPase subunit beta-3 | 99.8 | 98.9 |
| 301 CD299 | C-type lectin domain family 4 member M | 29.5 | 1.07 |
| 302 CD300a | CMRF35-like molecule 8 (CLM-8) | 1.82 | 0.222 |
| 303 CD300c | CMRF35-like molecule 6 (CML-6) | 37.3 | 3.76 |
| 304 CD300e | CMRF35-like molecule 2 (CML-2) | 38.7 | 0.697 |
| 305 CD301 | C-type lectin domain family 10 member A | 3.39 | 0.626 |
| 306 CD303 | C-type lectin domain family 4 member C | 66.8 | 3.33 |
| 307 CD304 | Neuropilin-1 (NRP-1) | 65.2 | 0.502 |
| 308 CD305 | Leukocyte-associated immunoglobulin-like receptor 1 (LIAR-1) | 4.12 | 0.972 |
| 309 CD307 | | 7.08 | 0.305 |
| 310 CD309 | VEGFR2/FLK-1/KDR | 34.4 | 14.2 |
| 311 CD312 | EGF-like module-containing mucin-like hormone receptor-like 2 | 24.8 | 12.2 |
| 312 CD314 | NKG2-D type II integral membrane protein | 38.5 | 11.6 |
| 313 CD317 | Bone Marrow Stromal Antigen 2 | 48.9 | 25 |
| 314 CD318 | CUB domain-containing protein 1 | 71.7 | 12.3 |
| 315 CD319 | SLAM family member 7 | 27.8 | 21.9 |
| 316 CD321 | Junctional adhesion molecule A (JAM-A) | 3.81 | 5.04 |
| 317 CD322 | Junctional adhesion molecule B (JAM-B/2) | 4.37 | 0.248 |
| 318 CD324 | Cadherin-1 | 17.2 | 0.387 |
| 319 CD325 | Cadherin-2/N-cadherin | 3.83 | 0.501 |
| 320 CD326 | Epithelial cell adhesion molecule (EPCAM) | 18.1 | 0.463 |
| 321 CD328 | Siglec-7 | 32 | 1.99 |
| 322 CD332 | FGFR2 | 0.814 | 0.181 |
| 323 CD333 | FGFR3 | 7.78 | 1.01 |
| 324 CD334 | FGFR4 | 1.35 | 1.76 |

TABLE 1-continued

Results of the HT-FACS analysis

| # | Marker | Alternative name: | % IMP | % Lonza® MSC |
|---|---|---|---|---|
| 325 | CD335 | NCR1 | 0.669 | 0.274 |
| 326 | CD336 | NCR2 | 0.544 | 0.212 |
| 327 | CD337 | | 87.3 | 26.4 |
| 328 | CD338 | ATP-binding cassette sub-family G member 2 | 49 | 19.5 |
| 329 | CD339 | Protein jagged-1 | 1.76 | 1.22 |
| 330 | CD340 | Receptor tyrosine-protein kinase erbB-2 | 94.9 | 41 |
| 331 | CD344 | Frizzled 4 | 65.5 | 17.5 |
| 332 | CD349 | Frizzled 9 | 87.6 | 80.3 |
| 333 | CD351 | FCAMR | 76.4 | 28.1 |
| 334 | CD352 | SLAM-6 | 0.518 | 0.394 |
| 335 | CD354 | TREM-1 | 13.6 | 1.66 |
| 336 | CD355 | Cytotoxic and regulatory T-cell molecule | 10.4 | 1.24 |
| 337 | CD357 | Tumor necrosis factor receptor superfamily member 18 | 10.4 | 1.95 |
| 338 | CD358/DR6 | | 45.1 | 7.63 |
| 339 | CD360 (BD) | | 24.9 | 3.53 |
| 340 | CD360 (BL) | | 33 | 4.5 |
| 341 | CD362 | Syndecan-2 | 14.7 | 0.774 |
| 342 | CD363 | Sphingosine 1-phosphate receptor 1 | 18.7 | 0.757 |
| 343 | CLA | | 0.277 | 9.23 |
| 344 | CLIP | | 0.138 | 0 |
| 345 | DCIR | | 0.264 | 0.15 |
| 346 | EGF-R | | 33.3 | 2.02 |
| 347 | FMC7 | | 0.0776 | 0 |
| 348 | HLA-ABC | | 99.9 | 99.8 |
| 349 | HLA-A2 | | 3.52 | 20.9 |
| 350 | HLA-DM | | 0.172 | 0.14 |
| 351 | HLA-DR | | 0.247 | 0.481 |
| 352 | HPC | | 2.14 | 6.31 |
| 353 | ITGB7 | | 0.34 | 0.159 |
| 354 | LTBR | Tumor necrosis factor receptor superfamily member 3 | 34.5 | 87.6 |
| 355 | MIC A/B | | 97.1 | 0.328 |
| 356 | Notch1 | | 20.5 | 4.01 |
| 357 | Notch2 | | 95.8 | 22.8 |
| 358 | Notch3 | | 5.37 | 2.15 |
| 359 | PAC-1 | | 0.137 | 0.971 |
| 360 | Podoplanin | | 8.81 | 2.91 |
| 361 | SSEA-3 | | 20.7 | 0.395 |
| 362 | SSEA-4 | | 87.4 | 2.44 |
| 363 | Stro-1 | | 18.5 | 6.27 |
| 364 | TCR alpha beta | | 0.327 | 0.195 |
| 365 | TCR gamma delta | | 52.9 | 11.1 |
| 366 | TPBG | | 0.197 | 0.178 |
| 367 | VB8 TCR | | 25.1 | 3.93 |
| 368 | VD2 TCR | | 13.2 | 12.1 |
| 369 | fMLP-R | | 11.4 | 0.641 |

Example 3

Luminex Assay

A luminex assay was used to quantitate different cytokines in the conditioned media from Lonza cells and IMP cell cultures. Data is shown in pg/ug of RNA, this is to standardise the data relevant to the number of cells in culture.

| Cytokine/ Chemokine | pg/ug RNA | | Result |
|---|---|---|---|
| | MSCs | IMPs | |
| IL-6 | 162.4 | 596 | Increase |
| IL-8 | 6.9 | 59.8 | Increase |
| IP-10 | 1.4 | 13.7 | Increase |
| MCP-1 | 75.8 | 322.5 | Increase |
| RANTES | 1.07 | 125.3 | Increase |
| IL-10 | 0.8 | 0.1 | Decrease |
| IL-12 (p70) | 41.6 | 21.9 | Decrease |

The invention claimed is:

1. A method of producing a population of IMP cells, comprising
   (a) physically separating mononuclear cells (MCs) from bone marrow and culturing the MCs for 15 to 25 days in a medium consisting essentially of alpha Minimum Essential Medium (MEM), L-alanyl-L-glutamine dipeptide, platelet lysate, and heparin, at 0% oxygen ($O_2$) supplied by an incubator and under conditions which allow the MCs to adhere to induce the MCs to differentiate into IMP cells and (b) harvesting and culturing the IMP cells in (a) to thereby produce the population, wherein harvesting comprises an antibody-based technique to select for a population in which
(i) at least 90% of the cells in the population express detectable levels of MIC A/B,
(ii) at least 60% of the cells in the population express detectable levels of CD304 (Neuropilin 1),
(iii) at least 45% of the cells in the population express detectable levels of CD178 (FAS ligand),
(iv) at least 10% of the cells in the population express detectable levels of CD289 (Toll-like receptor 9),
(v) at least 15% of the population express detectable levels of CD363 (Sphingosine-1-phosphate receptor 1),
(vi) at least 20% of the cells in the population express detectable levels of CD99,
(vii) at least 80% of the cells in the population express detectable levels of CD181 (C-X-C chemokine receptor type 1; CXCR1),
(viii) at least 30% of the cells in the population express detectable levels of epidermal growth factor receptor (EGF-R),
(ix) at least 60% of the cells in the population express detectable levels of CXCR2
(x) at least 5% of the cells in the population express detectable levels of CD126,
(xi) at least 90% of the cells in the population express detectable levels of HLA-ABC,
(xii) at least 90% of the cells in the population express detectable levels of CD340,
(xiii) the cells express detectable levels of CD83,
(xiv) the cells express detectable levels of CD86, and
(xv) 1% or fewer of the cells express detectable levels of CD70 and wherein the platelet lysate is produced by subjecting a population of human platelets to four freeze-thaw cycles, wherein the freeze portion of each cycle is carried out in liquid nitrogen.

2. A method according to claim 1, wherein the MCs are obtained from a patient or an allogeneic donor.

3. A method according to claim 1, wherein the antibody-based technique is fluorescent activated cell sorting (FACS) or magnetic bead separation.

* * * * *